United States Patent
Davidson

(10) Patent No.: US 11,052,064 B2
(45) Date of Patent: Jul. 6, 2021

(54) COMPOSITIONS, METHODS AND SYSTEMS FOR THE TREATMENT OF CUTANEOUS DISORDERS

(71) Applicant: Verrica Pharmaceuticals Inc., West Chester, PA (US)

(72) Inventor: Matthew Gene Davidson, Venice, CA (US)

(73) Assignee: Verrica Pharmaceuticals Inc., West Chester, PA (US)

(*) Notice: Subject to any disclaimer, the term of this patent is extended or adjusted under 35 U.S.C. 154(b) by 280 days.

(21) Appl. No.: 14/913,335

(22) PCT Filed: Aug. 21, 2014

(86) PCT No.: PCT/US2014/052184
§ 371 (c)(1),
(2) Date: Feb. 19, 2016

(87) PCT Pub. No.: WO2015/027111
PCT Pub. Date: Feb. 26, 2015

(65) Prior Publication Data
US 2016/0193177 A1 Jul. 7, 2016

Related U.S. Application Data

(60) Provisional application No. 61/868,525, filed on Aug. 21, 2013.

(51) Int. Cl.
*A61J 1/06* (2006.01)
*A61K 31/34* (2006.01)
(Continued)

(52) U.S. Cl.
CPC .................. *A61K 31/34* (2013.01); *A61J 1/06* (2013.01); *A61J 1/1418* (2015.05);
(Continued)

(58) Field of Classification Search
CPC ... A61J 1/418; A61J 1/06; A61J 1/065; A61K 31/34
See application file for complete search history.

(56) References Cited

U.S. PATENT DOCUMENTS 600,556 A * 3/1898 Schupphaus ............. C08K 5/06
106/169.5
4,143,050 A 3/1979 Rossy et al.
(Continued)

FOREIGN PATENT DOCUMENTS

CN 1966508 A 5/2007
CN 101012230 A 8/2007
(Continued)

OTHER PUBLICATIONS

International Search Report (ISR) in PCT/US2014/052184.
(Continued)

*Primary Examiner* — Tatyana Zalukaeva
*Assistant Examiner* — Jessica R Arble
(74) *Attorney, Agent, or Firm* — Wolf, Greenfield & Sacks, P.C.

(57) ABSTRACT

Devices, systems, methods, and kits for treating cutaneous diseases, such as warts, with a cantharidin formulation are generally described. The cantharidin formulations, described herein, may have many advantages over traditional cantharidin formulations, including removal of highly volatile and corrosive solvents, improved safety, and improved compatibility with common plastics for ease of delivery. The devices, systems, methods, and kits can be used for the precise application of the cantharidin formulation for the treatment of cutaneous diseases and other topical indications. Treatment of cutaneous diseases with cantharidin, using the devices, systems, methods, and/or kits may have many advantages over traditional therapies, including (Continued)

high single application efficacy, lack of scaring, and a mild pain profile.

48 Claims, 12 Drawing Sheets

(51) Int. Cl.
    *A61M 35/00*     (2006.01)
    *A61J 1/14*     (2006.01)
    *A61K 31/343*     (2006.01)
    *A61K 9/00*     (2006.01)
    *A61J 7/00*     (2006.01)
    *A61J 1/20*     (2006.01)

(52) U.S. Cl.
    CPC .......... *A61K 9/0014* (2013.01); *A61K 31/343* (2013.01); *A61M 35/003* (2013.01); *A61J 1/065* (2013.01); *A61J 1/201* (2015.05); *A61J 7/0053* (2013.01)

(56) References Cited

U.S. PATENT DOCUMENTS

| | | | |
|---|---|---|---|
| 4,148,874 A * | 4/1979 | Smith | A61K 9/0014 424/66 |
| 4,298,752 A | 11/1981 | Dauben et al. | |
| 4,895,727 A | 1/1990 | Allen | |
| 5,445,462 A | 8/1995 | Johnson et al. | |
| 5,590,780 A * | 1/1997 | O'Meara | B65D 1/09 206/520 |
| 6,066,124 A | 5/2000 | Caillouette | |
| D436,661 S | 1/2001 | Berry | |
| 6,547,467 B2 | 4/2003 | Quintero | |
| 6,673,031 B2 | 1/2004 | Mark | |
| 6,811,342 B2 | 11/2004 | Pauchet | |
| 8,518,076 B2 | 8/2013 | Stenton | |
| 8,871,801 B2 | 10/2014 | Levitt | |
| D771,250 S | 11/2016 | Zhang et al. | |
| D772,407 S | 11/2016 | Zhang et al. | |
| 9,480,691 B1 * | 11/2016 | Roth | A61K 8/63 |
| D801,830 S | 11/2017 | Zhang et al. | |
| 10,195,635 B2 | 2/2019 | Sporrer | |
| D868,160 S | 11/2019 | Lam | |
| 10,745,413 B2 | 8/2020 | Davidson et al. | |
| D900,312 S | 10/2020 | Davidson et al. | |
| 2003/0068331 A1 * | 4/2003 | Battaglia | A61P 31/10 424/195.18 |
| 2003/0072814 A1 | 4/2003 | Maibach et al. | |
| 2004/0162533 A1 | 8/2004 | Alley | |
| 2004/0242770 A1 * | 12/2004 | Feldstein | A61K 8/0208 525/54.3 |
| 2004/0254561 A1 | 12/2004 | Stenton | |
| 2005/0019418 A1 | 1/2005 | Crutchfield et al. | |
| 2005/0111900 A1 | 5/2005 | Fazzolari et al. | |
| 2005/0169696 A1 | 8/2005 | Albisetti | |
| 2006/0110415 A1 * | 5/2006 | Gupta | A61K 8/0212 424/401 |
| 2006/0180613 A1 | 8/2006 | Manesis | |
| 2007/0000566 A1 * | 1/2007 | Gueret | A45D 34/04 141/98 |
| 2007/0111954 A1 | 5/2007 | Crutchfield et al. | |
| 2007/0187437 A1 | 8/2007 | Lord | |
| 2007/0275045 A1 | 11/2007 | Evans et al. | |
| 2008/0146674 A1 * | 6/2008 | Rosenberg | A61K 9/0014 514/641 |
| 2008/0195040 A1 | 8/2008 | Clark et al. | |
| 2008/0246380 A1 * | 10/2008 | Gwak | F25D 23/025 312/405 |
| 2009/0311028 A1 | 12/2009 | Odermatt et al. | |
| 2011/0086109 A1 * | 4/2011 | Dever | A61K 47/14 424/642 |
| 2011/0208136 A1 | 8/2011 | Sollingen et al. | |
| 2011/0212033 A1 * | 9/2011 | Tamarkin | A61K 9/0014 424/43 |
| 2012/0016320 A1 | 1/2012 | Lin | |
| 2012/0148520 A1 * | 6/2012 | Strobel | A61K 31/422 424/78.06 |
| 2012/0312709 A1 * | 12/2012 | Kaufman | B65D 75/5822 206/370 |
| 2013/0004230 A1 | 1/2013 | Kirk et al. | |
| 2013/0197075 A1 * | 8/2013 | Levitt | A61K 31/34 514/468 |
| 2014/0275248 A1 * | 9/2014 | Johnson | A61K 31/14 514/535 |
| 2015/0118164 A1 | 4/2015 | Tamarkin et al. | |
| 2017/0305925 A1 | 10/2017 | Piotrowski et al. | |
| 2019/0002474 A1 | 1/2019 | Davidson et al. | |
| 2019/0031674 A1 | 1/2019 | Davidson et al. | |
| 2020/0155498 A1 | 5/2020 | Welgus et al. | |
| 2020/0270269 A1 | 8/2020 | Davidson et al. | |
| 2021/0070771 A1 | 3/2021 | Davidson et al. | |

FOREIGN PATENT DOCUMENTS

| | | |
|---|---|---|
| CN | 101108853 A | 1/2008 |
| CN | 101108854 A | 1/2008 |
| CN | 101108853 B | 5/2010 |
| CN | 101798309 A | 8/2010 |
| CN | 101036774 B | 12/2010 |
| CN | 102146086 A | 8/2011 |
| CN | 102336765 A | 2/2012 |
| CN | 102526146 A | 7/2012 |
| CN | 202730045 A | 2/2013 |
| CN | 202920809 | 5/2013 |
| CN | 202920809 U | 5/2013 |
| CN | 102268006 B | 8/2013 |
| EP | 0841059 A1 | 5/1998 |
| JP | H05-255367 A | 10/1993 |
| JP | 10-114626 | 5/1998 |
| JP | 10-114626 A | 5/1998 |
| JP | 11-319064 | 11/1999 |
| JP | 2004-059446 A | 2/2004 |
| JP | 2005-187330 | 7/2005 |
| JP | 2005-187330 A | 7/2005 |
| JP | 2010-516410 A | 5/2010 |
| JP | 2010-235471 A | 10/2010 |
| JP | 2013-507367 A | 3/2013 |
| WO | WO 2008/092068 A2 | 7/2008 |
| WO | WO 2010/079513 A2 | 7/2010 |
| WO | WO 2012/131238 A1 | 10/2012 |
| WO | WO 2015/027111 A1 | 2/2015 |
| WO | WO 2016/100732 A2 | 6/2016 |
| WO | WO 2016/134130 A1 | 8/2016 |
| WO | WO 2018/226894 A1 | 12/2018 |

OTHER PUBLICATIONS

Written Opinion of the International Search Authority in PCT/US2014/052184.
Rosenberg, E.W., et al., "Cantharidin Treatment of Warts at Home," Arch. Dermatol., vol. 113, p. 1134, Aug. 1977.
Bagatell, F.K., "Studies on Biological Factors in Acantholysis," The Journal of Investigative Dermatology, pp. 357-361 (1964).
Dormer Laboratories, "Cantharone and Cantharone Plus" sales brochure (publication date unknown).
Greico, et al., "Dramatic Rate Accelerations of Diels-Alder Reactions in 5 M Lithium Perchlorate-Diethyl Ether: The Cantharidin Problem Reexamined," J. Am. Chem. Soc., vol. 112, pp. 4595-4596 (1990).
Magyarosy, et al., "Cycloaddition Approach to the Curing of Polyimides via Precursor Containing Thiophene-S,S-dioxide," Heteroatom Chemistry, vol. 17, No. 7, pp. 648-652 (2006).
Extended European Search Report, dated Mar. 10, 2017, in connection with EP 14837297.2.
International Search Report and Written Opinion, dated Jul. 14, 2016, in connection with PCT/US2015/066487.
International Preliminary Report on Patentability, dated Jun. 29, 2017, in connection with PCT/US2015/066487.
International Preliminary Report on Patentability, dated Aug. 3, 2017, in connection with PCT/US2016/014139.

(56) References Cited

OTHER PUBLICATIONS

International Search Report and Written Opinion, dated Jul. 1, 2016, in connection with PCT/US2016/014139.
Aono et al., New method for generation of thiocarbonyl ylides from bis(trimethylsilylmethyl) sulfoxides and their application to cycloadditions. Heterocycles. 1995;40(1):249-60.
Cacchi et al., Palladium-catalyzed carbonylation of enol triflates. A novel method for one-carbon homologation of ketones to α,β-unsaturated carboxylic acid derivatives. Tetrahedron Letters. 26(8), 1985, pp. 1109-1112.
Dang et al., Determination of trace cantharidin in plasma and pharmacokinetic study in beagle dogs using gas chromatography-mass spectrometry. J Anal Toxicol. Sep. 2009;33(7):384-8.
Dauben et al., Organic reactions at high pressure. Cycloadditions with furans. J. Am. Chem. Soc. 1976;98(7):1992-1993.
Dauben et al., Organic reactions at high pressure. The preparative scale synthesis of cantharidin. J. Org. Chem. 1985;50 (14):2576-2578.
Dauben et al., Simple, efficient total synthesis of cantharidin via a high-pressure Diels-Alder reaction. J. Am. Chem. Soc. 1980;102(22):6893-6894.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Nikbakhtzadeh et al., Origin, transfer and distribution of cantharidin-related compounds in the blister beetle *Hycleus scabiosae*. J Venom Animals Toxins. 2012;18(1):88-96.
Rudo et al., Cantharidin—als Potenzmittel entzaubert, aber Oct. 1, 2013. Chemie in Unserer Zeit. vol. 47, Issue 5. With Supporting Information.
Schenck et al., Naturwissenshaften 1953, 40, 581.
Stork et al., A Stereospecific Synthesis of Cantharidin. J. Am. Chem. Soc., 1953;75(2):384-392.
Stork et al., Cantharidin. A Stereospecific Total Synthesis. J. Am. Chem. Soc. 1951;73(9):4501-4501.
Terao et al., Thiocarbonyl Ylides. VI. New Generation of Thiocarbonyl Ylides from Organosilicon Compounds Containing Sulfur and Their 1, 3-Cycloadditions. J-Stage. 1987;35(5):1734-1740.
White et al., Dihydrothiophenes as precursors to fused quinolines, quinolones and coumarins via o-quinodimethane intermediates. Tetrahedron 52(9), Feb. 26, 1996, pp. 3117-3134.
Invitation to Pay Additional Fees, dated Aug. 27, 2018, in connection with PCT/US2018/03653.
Supplementary European Search Report, dated Aug. 8, 2018, in connection with EP 16740681.8.
Invitation to Pay Additional Fees, dated Sep. 20, 2018, in connection with PCT/US2018/037808.
International Search Report and Written Opinion, dated Oct. 22, 2018, in connection with PCT/US2018/036353.
Extended European Search Report, dated Oct. 26, 2018, in connection with EP 15871116.8.
Extended European Search Report, dated Dec. 4, 2018, in connection with EP 16740681.8.
International Search Report and Written Opinion, dated Nov. 13, 2018, in connection with PCT/US2018/037808.
Invitation to Pay Additional Fees, dated Dec. 10, 2018, in connection with PCT/US2018/054373.
Aitken et al., Fragmentation patterns in the gas-phase pyrolysis of some bi- and tri-cyclic sulfolanes related to the 8-thiabicyclo[4.3.0]non-3-ene 8,8-dioxide ring system. J Chem Soc. Perkin Transactions 1. 1994;16:2301-2308.
Handy et al., Lithium Trifluoromethanesulfonimide in Acetone or Diethyl-ether as a Safe Alternative to Lithium Perchlorate in Diethyl-ether for Effecting Diels-alder Reactions. Unexpected Influence of the Counterion on Exo/endo Selectivity. Synlett 1995;5:565-567.
Hubbard et al., Lewis Acid Catalyzed Diels-Alder Reactions of Highly Hindered Dienophiles. J. Org. Chem. 1998;63(12):4143-4146.
Lange et al., Synthesis of 4-carboxy-2-thiabicyclo [3.2.0] Heptan-6-ones via 3-carboxy-2,3-dihydrothiophenes: potential β-lactamase inhibitors. Tetrahedron Lett. 1985;26(15):1791-1794.
International Preliminary Report on Patentability dated Dec. 26, 2019 in connection with International Application No. PCT/US2018/037808.
International Search Report and Written Opinion, dated Apr. 3, 2019 in connection with PCT/US2018/054373.
International Preliminary Report on Patentability dated Apr. 16, 2020, in connection with International Application No. PCT/US2018/054373.
[No Author Listed] CAS RN 27607-77-8. Entered STN: Nov. 16, 1984. 28 pages.
[No Author Listed] CAS RN 76262-87-8. Entered STN: Nov. 16, 1984. 19 pages.
[No Author Listed] CAS RN 89672-77-5. Entered STN: Nov. 16, 1984. 29 pages.
Anderson et al., Practical Process Research and Development. 1st Edition. Academic Press. Mar. 20, 2000. 81-111.
Auge et al., Catalysis by Lithium Cation: Lithium Trifluoromethanesulfonate as a Substitute for Lithium Perchlorate in Cycloadditions. Synlett 2000;6:877-9.
Bouacha et al., A theoretical study of the mechanism, stereoselectivity and Lewis acid catalyst on the Diels-Alder cycloaddition between furan and activated alkenes. Tetrahedron Letters. 2013;54:4030-4033.
Brion et al., On the lewis acid catalyzed diels-alder reaction of furan. regio- and stereospecific synthesis of substituted cyclohexenols and cyclohexadienols.Tetrahedron Letters. 1982;23(50):5299-302. https://doi.org/10.1016/S0040-4039(00)85823-2.
Hollis et al., Homogeneous catalysis. Titanium complex [Ti(Cp)2(CF3SO3)2] and zirconium complex [Zr(Cp)2(CF3SO3)2THF], efficient catalysts for the Diels-Alder reaction. Organometallics. Aug. 1, 1992;11(8):2745-8. https://doi.org/10.1021/om00044a004.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Houk et al, On Lewis Acid catalysis of diels-alder reactions. J Am Chem Soc. Jun. 13, 1973;95(12):4094-4096.
Huang, Catalysts for Hetero Diels-Alder Reaction of Imines. Chinese Journal of Organic Chemistry. Oct. 2003;23(10):1064-75.
Hunt et al., Why do catalytic quantities of lewis acid generally yield more product than 1.1 equiv in the intramolecular diels-adler reaction with a furan diene? Competitive complexation NMR studies provide an answer. J Am Chem Soc. 1995;117:1049-1056.
Kharitonov et al., Synthetic transformations of higher terpenoids: VIII. [4+2]-Cycloaddition reactions of lambertianic acid. Russian J Organic Chem. 2003;39(1):57-74.
Pagni et al., A chemical, spectroscopic, and theoretical assessment of the lewis acidity of LiClO4 in Diethyl Ether. J. Org Chem. 1993;58:3130-3133.
Prabhakar Reddy et al., Synthesis, cytotoxic activity and structure-activity relationships of hedychenone analogues. Bioorg Med Chem Lett. Apr. 15, 2010;20(8):2525-8. doi: 10.1016/j.bmcl.2010.02.101. Epub Mar. 3, 2010.
Song et al., Ionic liquids as powerful media in scandium triflate catalysed Diels-Alder reactions: significant rate acceleration, selectivity improvement and easy recycling of catalyst. Chem Commun. 2001;12:1122-3.
Sperry et al., Studies on the Diels-Alder reaction of annulated furans: application to the synthesis of substituted phenanthrenes. Tetrahedron Letters. Apr. 18, 2005;46(16):2789-93. Doi: 10.1016/j.tetlet.2005.02.148.
Tseng et al., Synthesis and Evaluation of Cantharidinimides on Human Cancer Cells. J Exp Clin Med. Oct. 2012;4(5):280-283.
Verma et al., Bioactive component, cantharidin from Mylabris cichorii and its antitumor activity against Ehrlich ascites carcinoma. Cell Biol Toxicol. Jun. 2012;28(3):133-47. doi: 10.1007/s10565-011-9206-6. Epub Mar. 9, 2012.
Kronemyer et al., Verrica develops a solution for common warts. Retrieved from www.dermatologytimes.com. Nov. 13, 2017. 1 page.

(56) References Cited

OTHER PUBLICATIONS

Extended European Search Report, dated Feb. 2, 2021, in connection with EP 18813599.0.
International Preliminary Report on Patentability, dated Dec. 19, 2019, in connection with PCT/US2018/036353.
Partial Supplementary European Search Report for Application No. EP 18864069.2, dated Apr. 12, 2021.
Baker et al., Biotin; the structure of 2-alkyldihydrothiophene-3,4-dicarboxylic acids. J Org Chem. Jan. 1948;13(1):123-33. doi: 10.1021/jo01159a017.
Moed et al., Cantharidin revisited: a blistering defense of an ancient medicine. Arch Dermatol. Oct. 2001;137(10):1357-60. doi: 10.1001/archderm.137.10.1357.
Opposition to Patent Application No. 252907 by Wavelength Enterprises, Ltd., filed Mar. 1, 2021. 78 pages.
Torbeck et al., Cantharidin: a comprehensive review of the clinical literature. Dermatol Online J. Jun. 15, 2014;20(6):13030/qt45r512w0.

\* cited by examiner

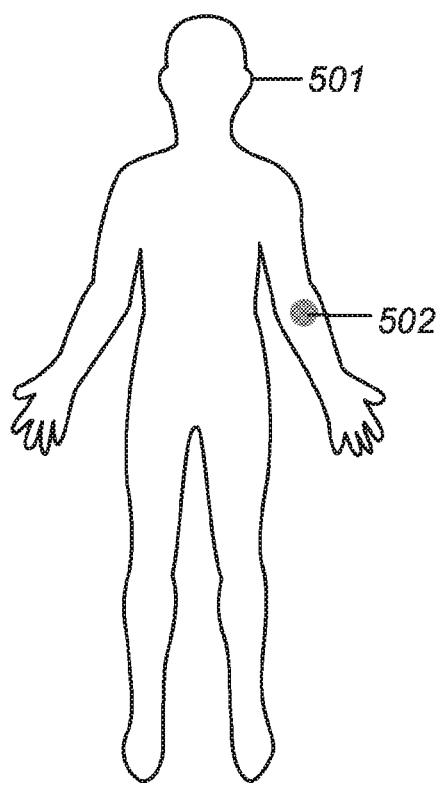
FIG. 5A
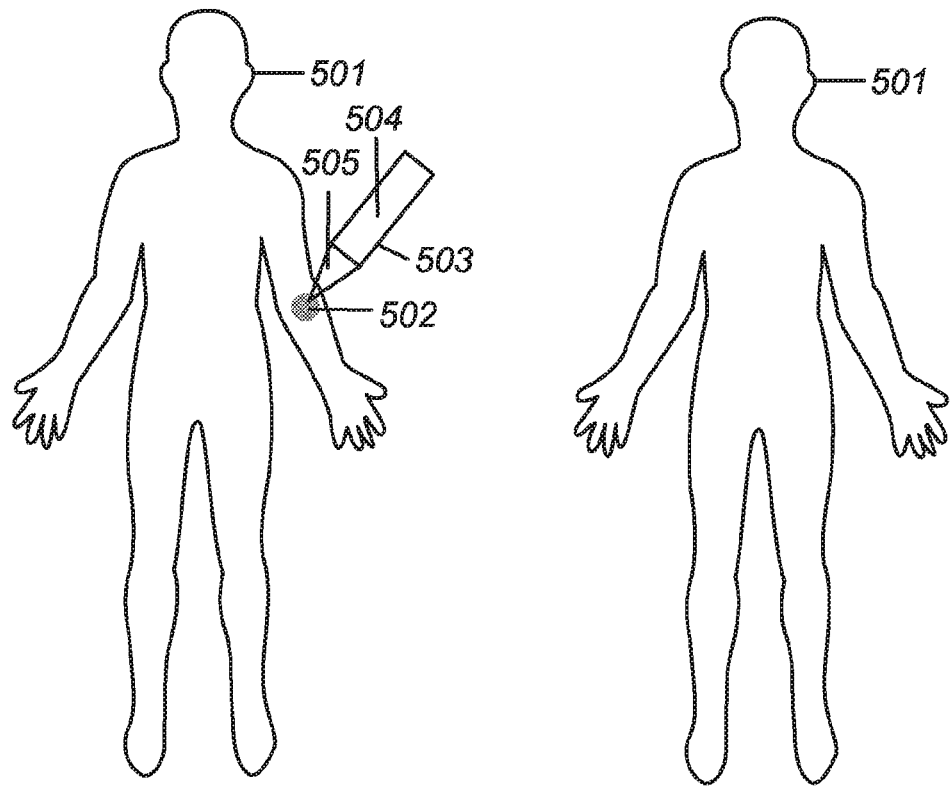
FIG. 5B
FIG. 5C

DETAIL
SCALE 4:1

SECTION

DETAIL
SCALE 4:1

SECTION

COMPOSITIONS, METHODS AND SYSTEMS FOR THE TREATMENT OF CUTANEOUS DISORDERS

RELATED APPLICATIONS

This application is a national stage filing under 35 U.S.C. § 371 of International PCT Application No. PCT/US2014/052184, filed Aug. 21, 2014, which claims priority to U.S. Provisional Application Ser. No. 61/868,525, filed Aug. 21, 2013, the entire contents of each of which is incorporated herein by reference.

BACKGROUND

Warts are small epidermal skin growths caused by viral infections, often found on the hands or feet. The most common type of wart is called *Verruca vulgaris*, which can be caused by multiple different strains of the Human papilloma virus (HPV). On most parts of the body these warts may be referred to as common warts; on the feet, however, they may be referred to as plantar warts when on the feet or genital warts or condoloma when on the genitals. Other epidermal viral conditions such as *Molluscum contagiosum* resemble warts but are caused by distinct viruses. These viral mediated skin growths may be unsightly and may have a significant risk for cancerous transformation and for spreading, making their removal desirable. Other superficial hyper-proliferative disorders resemble warts but are caused by non-viral mechanisms and include seborrheic keratosis, actinic keratosis and porokeratosis.

Multiple modalities have been used to remove warts and related diseases, including cryotherapy; surgical curettage; laser treatment; irritants such as salicylic acid and zinc oxide; acids such as nitric acid and squaric acid, immunotherapeutics such as imiquimod, 2,4-Dinitrochlorobenzene and candida antigen, and chemotherapeutics such as bleomyocin, podophyllotoxin and 5-fluorouracil. Many of these therapies can be painful, while others can leave disfiguring scars and/or require daily application. Perhaps most troubling, however, is that many of these cutaneous disorders remain recalcitrant even after multiple follow-up treatments. The small molecule cantharidin can be used to successfully treat these cutaneous disorders.

SUMMARY

The present disclosure provides formulations, devices, systems, methods and kits for treating skin conditions, such as warts. The present disclosure provides cantharidin formulations for treating warts and other cutaneous diseases. A cantharidin formulation can contain cantharidin, an intra-epidermal blistering agent. Cantharidin formulations of the present disclosure can have many advantages over traditional therapies, including high single application efficacy, lack of scaring, and a mild pain profile. Advantages of the cantharidin formulations herein over previously used cantharidin formulations include the removal of highly volatile and corrosive solvents, improved safety, and compatibility with common plastics for ease of delivery. Due to the nature of the solvents used in previously described cantharidin formulations, the application of cantharidin has been limited to glass containers which have a number of limitations. Devices provided herein can be used for the precise application of a cantharidin formulation for the treatment of warts and other topical indications.

An aspect of the present disclosure provides a system for delivering a cantharidin formulation to a subject comprising a reservoir and an applicator unit. The reservoir can comprise a cavity with the cantharidin formulation. The reservoir can have a volume less than or equal to about 10 milliliters (mL). The reservoir can be compressible to induce a pressure increase in the reservoir in excess of about 1.0 atmosphere (atm). The applicator unit can comprise an adaptor and an applicator tip. The applicator tip can comprise an opening and/or a channel in fluid communication with the reservoir. The applicator tip can be configured to transfer the cantharidin formulation from the reservoir to a location external to the applicator tip. The applicator unit can comprise a transparent cap that is configured to cover the applicator tip. The applicator unit can comprise a barrier on the opening. The transparent cap can comprise a puncture apparatus that is configured to puncture the barrier. The adaptor can lock into the screw cap of the reservoir. The opening of the applicator tip has a diameter less than or equal to 5 mm. The cantharidin formulation can comprise at least about 0.001% (w/v) cantharidin. In some cases, the cantharidin formulation can comprise at least about 0.01%, 0.1% or 1% cantharidin. The cantharidin formulation can comprise greater than or equal to 1% (w/v) of excipients. The reservoir can have a volume less than or equal to about 10 mL. The cantharidin formulation can comprises less than or equal to 5% (w/v) cantharidin, cantharidic acid, norcantharidin or palasonin combined. The subject can be diagnosed with a skin disease. The reservoir can have a screw cap on one end.

Another aspect of the present disclosure provides a system for delivering a cantharidin formulation comprising a cantharidin formulation and an applicator device. The cantharidin formulation can contain an excipient. The applicator device can be configured to deliver the cantharidin formulation. The cantharidin formulation comprises at least about 0.001% (w/v) cantharidin. In some cases, the cantharidin formulation can comprise at least about 0.01%, 0.1% or 1% cantharidin. The cantharidin formulation can comprise greater than or equal to 1% (w/v) of an excipient. The applicator device can comprise an applicator unit and one or more reservoirs. Each reservoir can comprise one or more cavities in fluid communication with the applicator unit. The reservoir can comprise a screw cap on one end. The reservoir can have a volume less than or equal to 5 mL. The reservoir can be compressible to induce a pressure increase in the reservoir in excess of about 1.0 atm. The applicator unit can comprise an applicator tip. The applicator tip can comprise an opening and/or an inner-channel in fluid communication with the reservoir. The applicator tip can be configured to transfer the cantharidin formulation from the reservoir to a location external to the applicator tip.

Another aspect of the present disclosure provides an applicator device for delivering a cantharidin formulation to a subject comprising an applicator unit and one or more reservoirs. The applicator unit can deliver the cantharidin formulation to the subject. The one or more reservoirs can each comprising one or more cavities in fluid communication with the applicator unit. At least one of the cavities can contain the cantharidin formulation. The reservoir can comprise a screw cap on one end. The reservoir can have a volume less than or equal to 5 mL. The reservoir can be compressible to induce a pressure increase in the reservoir in excess of about 1.0 atm. The applicator unit can comprise an applicator tip. The applicator can comprise an opening and/or an inner-channel in fluid communication with the reservoir. The applicator tip can be configured to transfer the cantharidin formulation from the reservoir to a location external to the applicator tip. An adaptor can be adjacent to the applicator tip, where the inner channel is directed from the applicator tip through the adaptor to the reservoir. The applicator unit can comprise a transparent cap that is configured to cover the applicator tip. The applicator unit can comprise a barrier on the opening, and wherein the transparent cap comprises a puncture apparatus that is configured to puncture the barrier. The adaptor can lock into the screw cap of the reservoir. The opening of the applicator tip can have a diameter less than or equal to about 5 mm. The cantharidin formulation can contain at least about 0.001% (w/v) cantharidin. In some cases, the cantharidin formulation can contain at least about 0.01%, 0.1% or 1% cantharidin. The cantharidin formulation can contain greater than or equal to about 1% (w/v) of an excipient. The reservoir can have a volume less than or equal to about 1 mL. The cantharidin formulation can contain less than or equal to about 5% (w/v) cantharidin.

Another aspect of the present disclosure provides a method for delivering a cantharidin formulation to a subject by providing an applicator device comprising a reservoir and an applicator unit, and delivering the cantharidin formulation from the reservoir to the subject. The reservoir can contain the cantharidin formulation. The applicator unit can comprise a channel in fluid communication with the reservoir. The cantharidin formulation can contain at least about 0.001% (w/v) cantharidin. In some cases, the cantharidin formulation can contain at least about 0.01%, 0.1% or 1% cantharidin. The cantharidin formulation can contain greater than or equal to about 1% (w/v) of excipient. The subject can be diagnosed with a skin disease. The skin disease can cause epithelial warts. The epithelial wart can be removed from the subject within two weeks after delivering the cantharidin formulation.

Another aspect of the present disclosure provides a method for treating epithelial warts, *Molluscum contagiosum* or other skin diseases in a subject by using an applicator device comprising a reservoir and an applicator unit to administer the cantharidin formulation to the subject. The reservoir can contain a cantharidin formulation. The applicator unit can be in fluid communication with the reservoir. The cantharidin formulation can contain at least about 0.001% (w/v) cantharidin. In some cases, the cantharidin formulation can contain at least about 0.01%, 0.1% or 1% cantharidin. The cantharidin formulation can contain greater than or equal to about 1% (w/v) of excipients. The epithelial lesions can be removed from the subject within two weeks after delivering the cantharidin formulation.

Another aspect of the present disclosure provides a kit for administering a cantharidin formulation to a subject. The kit can comprise a plurality of separately packaged, individually removable, dosage units in liquid or gel form. In some examples, a dosage unit is in a delivery device or system. In some cases, a dosage unit is in a packaging unit (e.g., ampule).

In some situations, a dosage unit can contain the cantharidin formulation in an amount from about 0.1 mL to about 10 mL. The cantharidin formulation contains at least about 0.001% of cantharidin. In some cases, the cantharidin formulation can contain at least about 0.01%, 0.1% or 1% cantharidin. The kit can be used for administering each of the active dosage units. The dosage units comprising the cantharidin formulation can be therapeutically effective for treating epithelial warts or other lesions in the subject. The kit can comprise at least three packaging units. The dosage unit containing the cantharidin formulation can be therapeutically effective in reducing epithelial warts or other lesions by at least about 50% in volume over the period of about 7 days.

Another aspect of the present disclosure provides instructions for the optimal treatment schedule. Different doses of cantharidin, the preparation of the skin, the frequency and quantity applied to the skin, how the skin is cared for after application and the amount of time cantharidin is left in contact with the skin have not been thoroughly tested by others and are not intuitively obvious to those skilled in the art as evidenced by the variability in peer-reviewed publications. The methods herein allow for the optimally effective treatment of warts, *Molluscum* and/or other cutaneous disorders with a cantharidin formulation.

Another aspect of the present disclosure provides a system for delivering a cantharidin formulation to a subject that can comprise a reservoir with at least one cavity with the cantharidin formulation, wherein the reservoir can have a volume less than or equal to about 10 milliliters (mL), and wherein the reservoir can be compressible to induce a pressure increase in the reservoir to a pressure in excess of about 1 atmosphere (atm). The system can further comprise an applicator unit that can include an adaptor and an applicator tip, wherein the applicator tip can comprise an opening and a channel in fluid communication with the reservoir, and wherein the applicator tip can transfer the cantharidin formulation from the reservoir to a location external to the applicator tip.

In some situations, the applicator unit can comprise a transparent cap that covers the applicator tip. In other situations, the applicator unit can comprise a barrier on the opening, and wherein the transparent cap may comprise a puncture apparatus that punctures the barrier. The opening of the applicator tip can have a diameter less than or equal to 5 millimeters (mm).

The cantharidin formulation can contain at least about 0.001% (w/v) cantharidin. In some cases, the cantharidin formulation can contain at least about 0.01%, 0.1% or 1% cantharidin. The cantharidin formulation can further contain greater than or equal to 1% (w/v) of excipients. The cantharidin formulation can further contain a flavorant and/or a colorant.

In some situations, the reservoir can have a volume less than or equal to about 10 mL and the cantharidin formulation can contain less than or equal to 5% (w/v) cantharidin, cantharidic acid, norcantharidin or palasonin combined. The reservoir can have a screw or snap-on cap on one end. The adaptor can lock into the screw or snap-on cap. The reservoir may be compressible to induce a pressure increase in the reservoir to a pressure that is less than about 10 atm.

Another aspect of the present disclosure provides a system for delivering a cantharidin formulation to a subject that can comprise a reservoir with a cantharidin formulation that can have at least about 0.001% (w/v) cantharidin and an excipient. The system can further include an applicator unit in fluid communication with the reservoir, wherein the application unit can deliver a volume less than or equal to about 10 milliliters (mL) of the cantharidin formulation.

The cantharidin formulation may contain at least about 0.01%, 0.1%, 0.5% or 1% cantharidin. The cantharidin formulation may further contain greater than or equal to about 0.001% (w/v), 0.01%, 0.1%, or 1% of the excipient.

In some situations, the reservoir may comprise a screw or snap-on cap on one end, (ii) can have a volume less than or equal to about 5 mL, and/or (iii) may be compressible to induce a pressure increase in the reservoir to a pressure in excess of about 1.0 atmosphere.

The applicator unit can comprise an applicator tip that can comprise an opening and an inner-channel in fluid communication with the reservoir, and wherein the applicator tip may transfer the cantharidin formulation from the reservoir to a location external to the applicator tip.

Another aspect of the present disclosure provides an applicator device for delivering a cantharidin formulation to a subject that can comprise one or more reservoirs each comprising one or more cavities, wherein at least one of the one or more cavities contains a cantharidin formulation. The applicator device can further include an applicator unit in fluid communication with the one or more reservoirs, wherein the applicator unit can controllably deliver a cantharidin formulation to a subject in an amount of no more than about 10 milliliters (mL) of the cantharidin formulation per use.

In some situations, the reservoir can comprise a screw or snap-on cap on one end, (ii) can have a volume less than or equal to about 5 mL, and/or (iii) may be compressible to induce a pressure increase in the reservoir to a pressure in excess of about 1.0 atmosphere. The applicator unit can comprise an applicator tip that that can comprise an opening and an inner-channel in fluid communication with the reservoir, and wherein the applicator tip may be configured to transfer the cantharidin formulation from the reservoir to a location external to the applicator tip.

In some situations, the applicator device can further comprise an adaptor adjacent to the applicator tip, wherein the inner channel is directed from the applicator tip through the adaptor to the reservoir. The applicator unit may comprise a transparent cap that may be configured to cover the applicator tip. The applicator unit can comprise a barrier on the opening, and wherein the transparent cap may comprise a puncture apparatus that may be configured to puncture the barrier. The adaptor may lock into the screw cap of the reservoir. The opening of the applicator tip can have a diameter less than or equal to about 5 mm.

In some situations, the cantharidin formulation may comprise at least about 0.0010% (w/v) cantharidin. The cantharidin formulation can comprise at least about 0.01%, 0.1% or 1% cantharidin. The cantharidin formulation may further comprise greater than or equal to about 1% (w/v) of an excipient. The reservoir can have a volume less than or equal to about 1 mL and the cantharidin formulation may contain less than or equal to about 5% (w/v) cantharidin.

Another aspect of the present disclosure provides a method for delivering a cantharidin formulation to a subject, comprising providing an applicator device that comprises (i) a reservoir that includes the cantharidin formulation and (ii) an applicator unit that comprises a channel in fluid communication with the reservoir, and delivering the cantharidin formulation from the reservoir through the channel to the subject.

The cantharidin formulation can contain at least about 0.001% (w/v) cantharidin. In some cases, the cantharidin formulation can contain at least about 0.01%, 0.1% or 1% cantharidin. The cantharidin formulation can further contain greater than or equal to about 1% (w/v) of excipient. The subject may be diagnosed with a skin disease. The skin disease may be exhibited as an epithelial wart. The epithelial wart can be removed from the subject within two weeks after delivering the cantharidin formulation.

In some situations, the application (or delivering) may comprise delivering less than or equal to about 10 milliliters (mL) of the cantharidin formulation. The application may comprise delivering less than or equal to about 5 mL of the cantharidin formulation. The application may comprise delivering less than or equal to about 4 mL of the cantharidin formulation. The application may comprise delivering less than or equal to about 3 mL of the cantharidin formulation. The application may comprise delivering less than or equal to about 2 mL of the cantharidin formulation. The application may comprise delivering less than or equal to about 1 mL of the cantharidin formulation.

Another aspect of the present disclosure provides a method for treating an epithelial wart (or other skin ailment) on a subject, comprising using an applicator device that comprises i) a reservoir that contains a cantharidin formulation and ii) an applicator unit in fluid communication with the reservoir to controllably administer the cantharidin formulation to the subject.

In some situations, the cantharidin formulation may contain at least about 0.001% (w/v) cantharidin. In some cases, the cantharidin formulation can contain at least about 0.01%, 0.1% or 1% cantharidin. The cantharidin formulation may further contain greater than or equal to about 1% (w/v) of excipient. The epithelial warts can be removed from the subject within two weeks after delivering the cantharidin formulation.

In some situations, the cantharidin formulation can be administered in a time period that is less than or equal to about 30 seconds. The cantharidin formulation can be administered in a time period that is less than or equal to about 20 seconds. The cantharidin formulation can be administered in a time period that is less than or equal to about 10 seconds. The cantharidin formulation can be administered in a time period that is less than or equal to about 5 seconds.

In some situations, the cantharidin formulation can be administered at a volume that is less than or equal to about 10 milliliters (mL) of the cantharidin formulation. In other situations, the cantharidin formulation can be administered at a volume that is less than or equal to about 5 mL of the cantharidin formulation.

Another aspect of the present disclosure provides a kit for administering a cantharidin formulation to a subject that comprises a plurality of separately packaged, individually removable, dosage units in liquid or gel form, wherein the dosage units can be in a packaging unit, wherein the dosage units each contains the cantharidin formulation in an amount from about 0.01 mL to 10 mL. The cantharidin formulation may contain at least about 0.001% (w/v) of cantharidin. In some cases, the cantharidin formulation can contain at least about 0.01%, 0.1% or 1% cantharidin.

In some situations, the kit can further include instructional material for administering the cantharidin formulation. The instructional material can enable the subject to self-administer the cantharidin formulation. The instructional material may be for treating an epithelial wart in the subject. The kit may comprise at least three packaging units. The cantharidin formulation can be suitable for removing an epithelial wart from the subject within two weeks after delivering the dosage unit comprising the cantharidin formulation.

Another aspect of the present disclosure provides a formulation that contains at least about 0.001% (w/v) of cantharidin, a flavorant that can induce a bitter taste in a subject upon ingestion of the formulation by the subject, and a colorant that can enable visible detection of the formulation by the subject. The formulation may have a volume of at most about 10 milliliters (mL).

In some situations, the cantharidin formulation may contain at least about 0.001% cantharidin. The cantharidin formulation may contain at least about 0.01%, 0.1%, 0.5% or 1% cantharidin. The flavorant and/or colorant can be at a concentration of at most about 1% (w/v). The volume can be less than or equal to about 5 mL. The formulation can have a Reynolds number less than about 1500 at 25oC. The formulation may further comprise a gelling agent. The formulation can have a manganese or magnesium ion concentration that is less than about 1%. The flavorant can be selected from the group consisting of denatonium, amarogentin, gentiopicrin, sucrose octaacetate, quercetin, brucine and quassin. The colorant can be selected from the group consisting of D&C violet, isosulfan blue, methylene blue, methyl red, methyl orange, congo red, alizarin yellow, bromocresol green and gentian violet.

Another aspect of the present disclosure provides a method for treating a skin ailment (e.g., wart) on a skin (or skin location) of a subject, comprising a) providing a cantharidin formulation that comprises (i) at least about 0.001% (w/v) of cantharidin, (ii) a flavorant that can induce a bitter taste in a subject upon ingestion of the formulation by the subject, and a colorant that can enable visible detection of the formulation by the subject, and b) providing the cantharidin formulation to the skin at a location that contains or is suspected of containing the skin ailment. The formulation can have a volume of at most about 10 milliliters (mL)

In some situations, the cantharidin formulation may contain at least about 0.001% cantharidin. The cantharidin formulation may contain at least about 0.01%, 0.1%, 0.5% or 1% cantharidin. The flavorant and/or colorant can be at a concentration of at most about 1% (w/v). The volume can be less than or equal to about 5 mL. The formulation can have a Reynolds number less than about 1500 at 25° C. The method may further comprise a gelling agent. The formulation can have a manganese or magnesium ion concentration that is less than about 1%. The flavorant can be selected from the group consisting of denatonium, amarogentin, gentiopicrin, sucrose octaacetate, quercetin, brucine and quassin. The colorant can be selected from the group consisting of D&C violet, isosulfan blue, methylene blue, methyl red, methyl orange, congo red, alizarin yellow, bromocresol green and gentian violet. The skin ailment can be selected from the group consisting of wart, *molluscum contagiosum*, seborrheic keratosis and actinic keratosis.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGs." herein) of which:

FIGS. 5A-5C schematically depict a method of treatment, in accordance with some embodiments of the present disclosure;

DETAILED DESCRIPTION

Figure 1A:
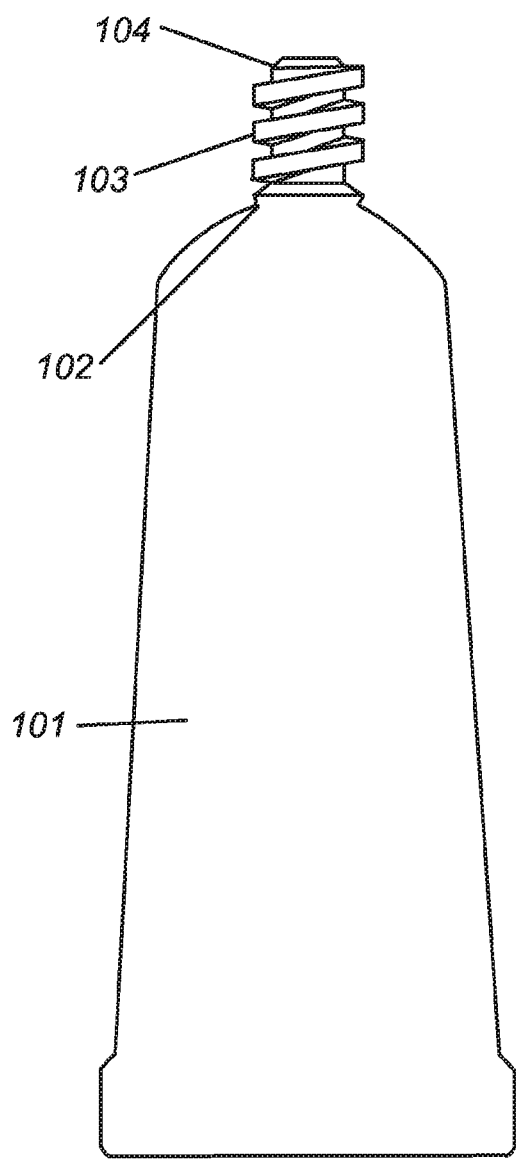
FIGS. 1A-1B schematically illustrate a reservoir for holding a cantharidin formulation, in accordance with some embodiments of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "treatment" or "treating," as used herein, generally refers to an approach for obtaining beneficial, predetermined or desired results, including, but not limited to, therapeutic benefit and/or a prophylactic benefit. By therapeutic benefit is meant eradication or amelioration of the underlying disorder being treated, such as a skin disease or ailment, such as warts. Also, a therapeutic benefit can be achieved with the eradication or amelioration of one or more of the physiological symptoms associated with the underlying disorder, such that an improvement is observed in the patient, notwithstanding that the patient may still be afflicted with the underlying disorder. Treatment can include diagnosis of a health condition, such as warts.

The term "cantharidin," as used herein, generally refers to a compound of the structure below, or a derivative thereof that has similar activity with regard to protein phosphatase inhibition. Compounds in which boron has been substituted in place of carbon may also be considered cantharidin. Compounds with differing proportions of carbon isotopes may also be considered cantharidin (e.g., $C^{14}$). Compounds with differing proportions of oxygen isotopes may also be considered cantharidin (e.g., $O^{17}$). Compounds with different proportions of hydrogen isotopes may also be considered cantharidin ($H^3$). Compounds with different proportions of carbon, oxygen, hydrogen isotopes or combinations thereof may also be considered cantharidin. Cantharidin may comprise one or more unstable radioactive elements. Cantharidin may not comprise one or more unstable radioactive elements. Cantharidin may comprise a pharmaceutically acceptable salt. Cantharidin may not comprise a pharmaceutically acceptable salt.

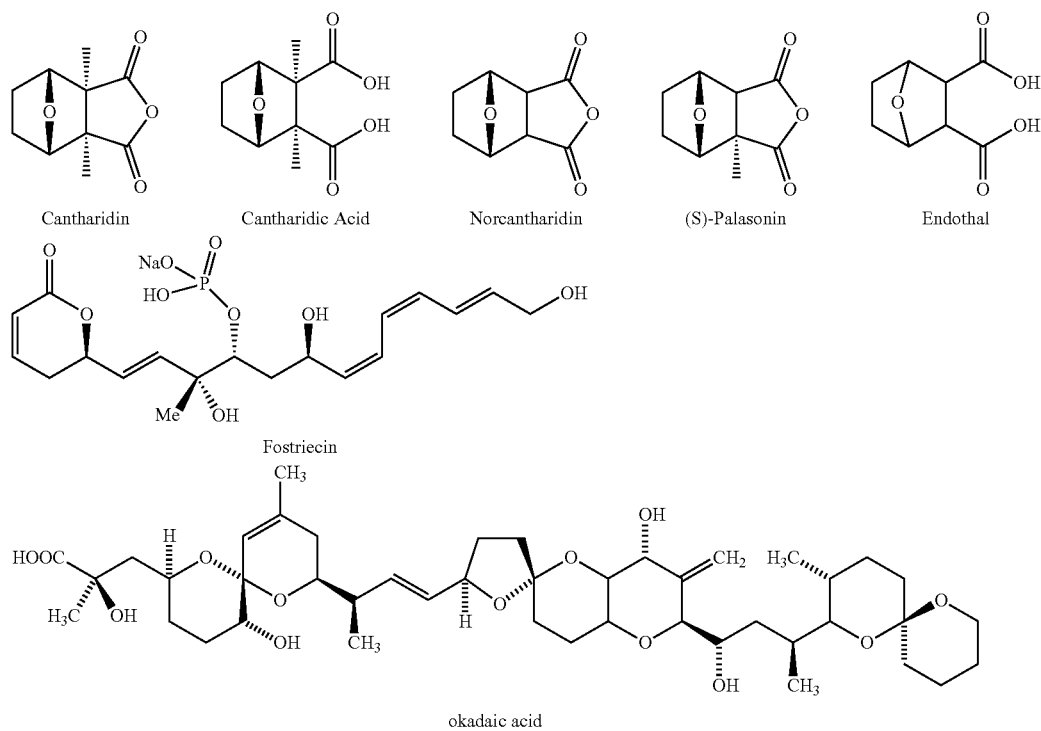

Cantharidin    Cantharidic Acid    Norcantharidin    (S)-Palasonin    Endothal

Fostriecin okadaic acid

Non-limiting examples of cantharidin derivatives include cantharidic acid, norcantharidin, palasonin, endothal, fostriecin and okadaic acid (see above). Other species with or without substitutions that have an exo,exo-dicarbolic acid or which may be expected to breakdown or be metabolized into the species containing an exo,exo-dicarbolic acid may also be considered "cantharidin". Other compounds that serve as inhibitors of protein phosphatases 1, 2A, 4 or 5 may also be considered "cantharidin." A cantharidin formulation can comprise cantharidin alone or in addition to one or more other species, such as one or more excipients.

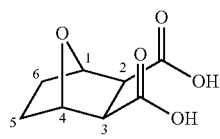

Non limiting examples of substituted exo,exo-dicarbolic acids include: 2,3-trimethylene anhydride; unsubstituted-anhydride; 5,6-dehydro-anhydride; endo-5-methyl; mono-4-chloranilide; endo-5-carboxy; 5,6-dehydro; 2-bromo; endo-5-hydroxymethyl.

Cantharidin may be produced by one or more blister beetles including but not limited to Spanish fly beetles, false blister beetles, cardinal beetles, soldier beetles, Chinese blister beetles or combinations thereof. The amount of cantharidin produced per blister beetle may be about 0.1, 0.2, 0.3, 0.4, 0.5, 0.6, 0.7, 0.8, 0.9, 1, 1.5, 2, 2.5, 3, 3.5, 4, 4.5, 5, 5.5, or about 6 mg. The amount of cantharidin produced per blister beetle may be more than about 0.1, 0.2, 0.3, 0.4, 0.5, 0.6, 0.7, 0.8, 0.9, 1, 1.5, 2, 2.5, 3, 3.5, 4.4.5, 5, 5.5, 6 mg or more. The amount of cantharidin produced per blister beetle may be less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6 mg or less. Cantharidin may be produced by biosynthesis. In some cases, biosynthesis of derivatives of cantharidin, norcantharidin, cantharidimide, or norcantharimide produces similar therapeutic effects in the user or patient. As an alternative, cantharidin can be produced fully synthetically or semi-synthetically, for example, using naturally occurring raw materials.

The term "excipient," as used herein, generally refers to an inactive ingredient as part of a formulation. Examples of excipients include, without limitations, dyes, flavors, binders, emollients, fillers, lubricants, antioxidants, skin penetration enhancers and preservatives. In some cases, an excipient can be selected from lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. In some embodiments, an excipient can be salicylic acid and/or podophyllotoxin.

The term "user," as used herein, generally refers to an individual using a delivery device or system to administer a cantharidin formulation to her or himself, or another individual, such as a subject.

The term "subject," as used herein, generally refers to an individual that is suspected of having an ailment (e.g., skin ailment), that has been diagnosed with the ailment, or is under treatment. For example, a subject can be under treatment by another individual or being administered a cantharidin formulation of the disclosure, either by him or herself or by another individual, such as a healthcare provider (e.g., physician, treating physician, physician's assistant, nurse) or a care provider. A subject can include asymptomatic individuals and symptomatic individuals, such as a patient. In some cases, the subject can be diagnosed with a skin disease.

The term "about" as used herein refers to within plus or minus (+/−) 10%, 9%, 8%, 7%, 6%, 5%, 4%, 3%, 2%, or 1% of the designated amount.

Cantharidin Formulations

An aspect of the present disclosure provides cantharidin formulations for treating skin conditions, ailments and/or diseases, such as cutaneous warts. A cantharidin formulation can include a therapeutically effective amount of cantharidin.

In some cases, a cantharidin formulation for topical delivery comprises cantharidin and excipients suitable for topical delivery of cantharidin to a subject. The amount of cantharidin in the cantharidin formulation is not particularly limited. The amount of a formulation may be limited to a therapeutic amount. In some circumstances, it may be advantageous to include amounts of cantharidin far in excess of nominal therapeutic amounts, for example to maximize the concentration of cantharidin. In other embodiments, it may be advantageous to limit the amounts of cantharidin based on toxicity to the subject.

In some cases, a cantharidin formulation can comprise at least about 50% (w/v) of cantharidin, at least about 10% (w/v) of cantharidin, at least about 5% (w/v) of cantharidin, at least about 1% (w/v) of cantharidin, at least about 0.75% (w/v) of cantharidin, at least about 0.5% (w/v) of cantharidin, at least about 0.1% (w/v) of cantharidin, at least about 0.01% (w/v) of cantharidin, or at least about 0.001% (w/v) of cantharidin. Cantharidin may be present in an amount between about 0.001% and 50% by weight, or between about 1% and about 10% by weight, or between about 0.001% and 1% by weight. Cantharidin may be present in an amount of about 0.001, 0.01, 0.1, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 grams per ml. Cantharidin may be present in an amount of more than about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15 grams or more per ml. Cantharidin may be present in an amount of less than about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15 grams or less per ml.

A cantharidin formulation can have a cantharidin concentration (milligram (mg) cantharidin/milliliter (mL) formulation) of about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg mL, 4.8 mg/mL, 4.9 mg mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg/mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg/mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some examples, the cantharidin concentration is an amount of 0.5 milligrams (mg) to 20 mg per milliliter (ml), or 1 mg to 10 mg per ml.

As an alternative, a cantharidin formulation can have a cantharidin concentration (mg cantharidin/mL formulation) of at least about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some situations, the cantharidin formulation can have a cantharidin concentration that is less than or equal to about 40 mg/mL, 30 mg/mL, 20 mg/mL, 10 mg/mL, 5 mg/mL, or 1 mg/mL.

The cantharidin used in the formulation may be of sufficient purity to induce a therapeutic effect without associated toxicity. Purity of the cantharidin used in the formulation may be between 50% and 100%. The purity of the cantharidin used may be greater than or equal to about 70%, 80%, 90%, 95%, 98%, 99%, or 99.9%.

In some embodiments, cantharidin can be formulated into preparations in solid, semi-solid, gel, or liquid forms suitable for local or topical administration, such as gels, water-soluble jellies, creams, lotions, suspensions, solutions, foams, powders, slurries, ointments, solutions, oils, capsules, tablets, pastes, suppositories, sprays, emulsions, saline solutions, dimethylsulfoxide (DMSO)-based solutions, suitable for local or topical administration. Carriers with high densities may be capable of providing an area with a prolonged exposure to the active ingredients. In contrast, a solvent/solution formulation may provide more immediate exposure of cantharidin to the chosen area.

A cantharidin formulation may also comprise suitable solid, semi-solid, gel or liquid phase carriers or excipients, which are compounds that may provide increased penetration of, or modify the delivery of, therapeutic molecules across the stratum corneum permeability barrier of the skin. Examples of such carriers and excipients include, but are not limited to, destructive agents (e.g., bases, acids, oxidizers), crosslinking agents (e.g. formalin or formaldehyde), humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

A cantharidin formulation can contain and acid or combination of acids, including, but not limited to, salicylic acid, trichloroacetic acid, hydrochloric acid, formic acid, squaric acid or nitric acid. A cantharidin formulation can contain podophyllotoxin. A cantharidin formulation can contain zinc oxide. A cantharidin formulation can contain immunotheraputics such as imiquimod, 2,4-Dinitrochlorobenzene and/or candida antigen. A cantharidin formulation can contain chemotherapeutics such as bleomyocin, podophyllotoxin and/or fluorouracil. A cantharidin formulation can contain an oxidizer, such as hydrogen peroxide.

A cantharidin formulation can include a solubilizer to ensure good solubilization and/or dissolution of cantharidin and to minimize precipitation of cantharidin in the formulation. A solubilizer may be added to increase the solubility of cantharidin and/or to maintain the composition as a stable or homogeneous solution, emulsion or dispersion.

Examples of suitable solubilizers include, but are not limited to, one or more of the following: alcohols and polyols, such as acetone, ethanol isopropanol, butanol, benzyl alcohol, ethylene glycol, propylene glycol butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose, hydroxyethylcellulose, hyroxypropylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, □-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof; δ-valerolactone and isomers thereof, β-butyrolactone and isomers thereof; and other solubilizers, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, polyethylene glycol 200-100, glycofurol, transcutol, propylene glycol dimethyl isosorbide, sorbitol, glycerol, triacetin, ethyl alcohol, PEG-400, glycofurol and propylene glycol.

The amount of a given solubilizer may be limited to a bio-acceptable amount. In some circumstances, it may be advantageous to include amounts of solubilizers in excess of bioacceptable amounts, for example to maximize the concentration of the drug, with excess solubilizer removed prior to providing the composition to a subject using conventional techniques, such as distillation or evaporation. A solubilizer, if present, can be in a weight ratio of 10%, 25%, 50%, 100%, or up to about 200% by weight, based on the combined weight of cantharidin, and other excipients. As an alternative, substantially low amounts of solubilizer may also be used, such as 5%, 2%, 1% or even less by weight of the cantharidin formulation. In some examples, the solubilizer may be present in an amount of about 1% to about 100%, or about 5% to about 25% by weight of the cantharidin formulation. In some cases, a cantharidin formulation includes less than a bio-acceptable amount.

A cantharidin formulation can comprise one or more film-forming agents. A cantharidin formulation may not comprise one or more film-forming agents. Some examples of film-forming agent may include but are not limited to nitrocellulose, nitrocellulose derivatives, polyvinyl pyrrolidone, hydroxypropylmethycellulose, carboxymethylcellulose and other film-forming agents or combinations thereof. The film-forming agent may be dissolved in a solvent. The film-forming agent may be dissolved in one or more solvents. A cantharidin formulation may include one or more solvents. The solvent may be ethanol, acetone, methanol, isopropyl alcohol, butyl alcohol, pentanol, ether, water or other solvents. In some cases, the solvent is not or does not include diethyl ether. The solvent may be acetone. A cantharidin formulation may comprise one or more plasticizers. A cantharidin formulation may not comprise one or more plasticizers. Examples of such plasticizers may include but are not limited to camphor and castor oil. A cantharidin formulation can comprise one or more water-mediated polymerization agents. A cantharidin formulation may not comprise one or more water-mediated polymerization agents. Examples of water-mediated polymerization agents may include, but are not limited to, 2-octyl cyanoacrylate and butyl cyanoacrylate. In some cases, including a film-forming agent, a plasticizer, a water-mediated polymerization agent or combinations thereof, provides a final cantharidin formulation with viscosity, flexibility, durability, rigidity, ruggedness and or film-forming properties.

In some cases, one or more film-forming agents are present in a cantharidin formulation at a weight-to-volume concentration of between about 0.1% to about 10%. In some cases, one or more film-forming agents is present in a cantharidin formulation at a weight-to-volume concentration of about 1.25%. In some cases, one or more film-forming agents are present in a cantharidin formulation at a weight-to-volume concentration of about 2%. In some cases, one or more film-forming agents is present in a cantharidin formulation at a weight-to-volume concentration of about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25%. In some cases, one or more film-forming agents is present in a cantharidin formulation at a weight-to-volume concentration of more than about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25% or more. In some cases, one or more film-forming agents is present in a cantharidin formulation at a weight-to-volume concentration of less than about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25% or less.

In some cases, the one or more solvents is present in a cantharidin formulation at a weight-to-volume concentration of between about 10% to about 95%. In some cases, the one or more solvents is present in a cantharidin formulation at a weight-to-volume concentration of about 13%. In some cases, the one or more solvents is present in a cantharidin formulation at a weight-to-volume concentration of about 87%. In some cases, the one or more solvents is present in a cantharidin formulation at a weight-to-volume concentration of about 10, 15, 20, 25, 30, 35, 40, 45, 50, 55, 60, 65, 70, 75, 80, 85, 90, or 95%. In some cases, the one or more solvents is present in a cantharidin formulation at a weight-to-volume concentration of more than about 10, 15, 20, 25, 30, 35, 40, 45, 50, 55, 60, 65, 70, 75, 80, 85, 90, 95% or more. In some cases, the one or more solvents is present in a cantharidin formulation at a weight-to-volume concentration of less than about 10, 15, 20, 25, 30, 35, 40, 45, 50, 55, 60, 65, 70, 75, 80, 85, 90, 95% or less.

When applied to the skin, a cantharidin solution can dry rapidly, such as, e.g., within 1 second, 10 seconds, 30 seconds, 1 minute, 5 minutes or 10 minutes. In an example, an assay used to evaluate the drying time of a cantharidin formulation is to apply 4 microliters of cantharidin formulation evenly over a 3 mm diameter circle of skin with a pipette. In an example, the cantharidin formulation dries in less than 2 minutes or 30 seconds.

In some cases, the one or more plasticizers are present in a cantharidin formulation at a weight-to-volume concentration of between about 0.001% to about 5%. In some cases, a plasticizer is not present in a cantharidin formulation. In some cases, the one or more plasticizers is present in a cantharidin formulation at a weight-to-volume concentration of about 5% or less. In some cases, a plasticizer is present in a cantharidin formulation at a weight-to-volume concentration of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 5%. In some cases, a plasticizer is present in a cantharidin formulation at a weight-to-volume concentration of more than about 0.001, 0.01 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5% or more. In some cases, a plasticizer is present in a cantharidin formulation at a weight-to-volume concentration of less than about 0.001, 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5% or less.

A cantharidin formulation can comprise a dye. A cantharidin formulation may comprise one or more dyes. A cantharidin formulation may not comprise a dye. A dye may be an acridine, anthraquinone, arylmethane, azo, diazonium, nitro, phtalocyanine, quinone imine, tetrazolium, thiazole, xanthene, acid, basic, direct, mordant, natural or solvent dye used at a concentration sufficient to adjust the color of the cantharidin formulation.

A dye may be acridine orange, acriflavine, anthracene blue SWR, alizarin, alizarin red S (mordant red 3), nuclear fast red, auramine O, chromoxane cyanin R, pararosanilin, rosanilin, magenta II, new fuchsin, methyl violet 2B, methyl violet 6B, crystal violet, Hoffman's violet, methyl green, ethyl green, acid fuchsin (acid violet 19), fast red B, fast blue B, diazonium chloride, diazonium acid sulphate, diazonium alkyl sulphate, diazonium chloride, diazonium fluborates, or diazonium benzenesulphonates, picric acid, alcian blue, luxol fast blue, toluidine blue O, thionin, azure A, azure B, azure C, neutral red, safranin O, gallocyanin, gallamin blue, iodonitrotetrazolium, nitro blue tetrazolium, thioflavine T, pyronin Y, pyronin B, rhodamine B, martius yellow (acid yellow 24), eosin Y (acid red 87), biebrich scarlet (acid red 66), suphonated pararosanilin (basic red 9), pararosanilin (basic red 9), methylene blue (basic blue 9), congo red (direct red 28), erie garnet (direct red 10), sirius red F3B (direct red 80), hematein (natural black 1), chromoxane cyanine R (mordant blue 3), celestine blue B (mordant blue 14), kermes (natural red 3), carmine (natural red 3), lac (natural red 25), hematein (natural black 1), saffron (natural yellow 6), sudan III (solvent red 23), sudan IV (solvent red 24), oil red O (solvent red 27), sudan black B (solvent black 3), or others.

A dye can include a phase change dye. A dye may include more than one phase change dye. A dye may not include a phase change dye. Some examples of phase changes dyes may include but are not limited to D&C orange, neozapon red 492, orasol red G, direct brilliant pink B, direct red 3BL, supranol brilliant red 3BW, lemon yellow 6G, light fast yellow 3G, aizen spilon yellow C-GNH, bemachrome yellow GD sub, cartasol brilliant yellow 4GF, cibanone yellow 2G, orasol black RLI, orasol black CN, savinyl black RLSN, pyrazol black BG, morfast black 101, diaazol black RN, thermoplast blue 670, orasol blue GN, savinyl blue GLS, luxol fast blue MBSN, sevron blue 5GMF, basacid blue 750, keyplast blue, neozapon black X51, classic solvent black 7, sudan blue 670, sudan yellow 146, sudan red 462, ncptune red base NB543, ncopcn blue FF-4012, fatsol black BR, morton morplas magenta 36, or others.

A dye can include serve as an indicator dye. A dye may include more than one indicator dye. A dye may not include an indicator dyes. Some examples of indicator dyes may include but are not limited to D&C violet, isosulfan blue, methylene blue, methyl red, methyl orange, congo red, alizarin yellow, bromocresol green, gentian violet, or others. A dye can include one or more phase change dyes and one or more indicator dyes or combinations thereof. Indicator dye(s) can be used at a concentration sufficient to demark the area treated with a cantharidin formulation.

A cantharidin formulation can contain a fluorophore. A cantharidin formulation may contain more than one fluorophorc. A cantharidin formulation may not contain a fluorophore. A fluorophore may indicate the presence of a mineral (e.g., magnesium, calcium, zinc, copper, iron, lead, cadium, mercury, nickel, cobalt, aluminum, or lanthanides). A fluorophore may indicate the presence of magnesium. A fluorophore may indicate the presence of intracellular magnesium. A cantharidin formulation may contain a fluorophore that fluoresces under an ultra violet light. Examples of fluorescent indicators that fluoresce under ultra violet light may include but are not limited to mag-indo-1 or mag-fura-2. A cantharidin formulation may contain a fluorophore that fluoresces under visible light. Examples of fluorescent indicators that fluoresce under visible light may include but are not limited to magnesium green or mag-fluo-4.

A cantharidin formulation can comprise one or more fluorophores, one or more dyes, or combinations thereof. In some cases, the one or more fluorophores or one or more dyes is present in a cantharidin formulation in a weight-to-volume concentration of about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07. 0.08, 0.09, 0.1, 0.2, 0.3, 0.4, 0.5, 0.6, 0.7, 0.8 0.9, 1, or 10%. In some cases, the one or more fluorophores or one or more dyes is present in a cantharidin formulation in a weight-to-volume concentration of more than about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8 0.9, 1, 10% or more. In some cases, the one or more fluorophores or one or more dyes is present in a cantharidin formulation in a weight-to-volume concentration of less than about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8 0.9, 1, 10% or less. In some cases, the one or more fluorophores or one or more dyes is present in a cantharidin formulation in a weight-to-volume concentration of between about 0.00001% and about 1%. In some cases, the one or more fluorophores or one or more dyes is present in a cantharidin formulation in a weight-to-volume concentration of about 0.005%.

A cantharidin formulation can contain one or more aversive agents such as bittering agents or oral deterrents. A bittering agent is an example of a flavorant. A bittering agent or oral deterrent can be used to prevent or deter oral ingestion of the formulation. A bittering agent or oral deterrent can be used to prevent or deter licking and/or ingestion of the formulation prior to, during or after it has been applied to the skin. Bittering agents or oral deterrents can include, but are not limited to, denatonium (e.g., denatonium benzoate, denatonium saccharide), amarogentin, gentiopicrin, sucrose octaacetate, quercetin, brucine, and quassin. Bittering agent, denatonium benzoate may be added to a cantharidin formulation.

An aversive agent may be present in a cantharidin formulation in a concentration of about 0.01, 0.02, 0.03, 0.04, 0.05, 0.06, 0.07, 0.08, 0.09, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 parts per million (ppm). In some cases, an aversive agent is present in a cantharidin formulation in a concentration of more than about 0.01, 0.02, 0.03, 0.04, 0.05, 0.06, 0.07, 0.08, 0.09, 1, 1.5, 2, 2.5, 3, 3.5, 4, 4.5, 5, 5.5.6, 6.5, 7, 7.5, 8, 8.5, 9, 9.5, 10, 11, 12, 13, 14, 15, 16, 17, 18, 19, 20 ppm or more. In some cases, an aversive agent is present in a cantharidin formulation in a concentration of less than about 0.01, 0.02, 0.03, 0.04, 0.05, 0.06, 0.07, 0.08, 0.09, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 ppm or less. In some cases, an aversive agent is present in a cantharidin formulation in a concentration of between about 0.01 ppm to about 20 ppm.

In some cases, an aversive agent is present in a cantharidin formulation in a weight-to-volume concentration of about 0.00001% to about 1% of the total liquid volume. In some cases, an aversive agent is present in a cantharidin formulation in a weight-to-volume concentration of about 0.000001%, 0.00001%, 0.0001%, 0.001%, 0.01%, 0.1%, 1%, or about 2%. In some cases, an aversive agent is present in a cantharidin formulation in a weight-to-volume concentration of more than about 0.000001%, 0.00001%, 0.0001%, 0.001%, 0.01%, 0.1%, 1%, 2% or more. In some cases, an aversive agent is present in a cantharidin formulation in a weight-to-volume concentration of less than about 0.000001%, 0.00001%, 0.0001%, 0.001%, 0.01%, 0.1%, 1%, 2% or less. An aversive agent may be present in a cantharidin formulation in a weight-to-volume concentration of about 0.0006%. An aversive agent may be present in a cantharidin formulation in a weight-to-volume concentration of about 0.0001% to about 0.001%.

A cantharidin formulation can include one or more pharmaceutically acceptable additives or excipients. Such additives or excipients can include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In some cases, a cantharidin formulation can have a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0. As an alternative, a cantharidin formulation can have a pH of at least about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0.

A cantharidin formulation may be in liquid form. The liquid form may have a resistance to fluid flow. The liquid form may have a Reynolds number less than about 4000, 3000, 2000, 1500, 1000, 500, 400, 300, 200, or 100. The liquid form may have a Reynolds number that is about 0.1, 1, 5, 10, 25, 50, 75, 100, 250, 500, 1000, 1250, 1500, 1750, or about 2000. The liquid form may have a Reynolds number that is less than about 2000, 1750, 1500, 1250, 1000, 500, 400, 300, 250, 200, 150, 100, 75, 50, 25, 10, 5, 1, 0.1 or less.

In some cases, a cantharidin formulation may have a Reynolds number less than about 4000, 3000, 2000, 1500, 1000, 500, 400, 300, 200, or 100 at a temperature of about 25° C. The liquid form may have a Reynolds number that is about 1, 5, 10, 25, 50, 75, 100, 250, 500, 1000, 1250, 1500, 1750, or about 2000 at a temperature of about 25° C. The liquid form may have a Reynolds number that is less than about 2000, 1750, 1500, 1250, 1000, 500, 400, 300, 250, 200, 150, 100, 75, 50, 25, 10, 5, 1 or less at a temperature of about 25° C.

The liquid form may have a high viscosity. The liquid form may be substantially viscous such that the liquid may not splash, drip, run, drain, leak, aerosolize out of the applicator unit. The liquid form may be substantially viscous such that the cantharidin formulation remains at the location on the patient or on the user where it was administered. The liquid form may be substantially viscous such that the cantharidin formulation may not flow, splash, drip, run, drain, or leak from the location on the patient or on the user where it was administered.

One or more gelling agents may be added to the liquid form to increase viscosity, for example, dextran, nitrocellulose, hydroxypropyl cellulose, ethyl cellulose, or others. The viscosity of the liquid form at ambient conditions (e.g., 25° C.) may be about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, or about 2,000,000 centipoise. The viscosity of the liquid form at ambient conditions may be more than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or more. The viscosity of the liquid form at ambient conditions may be less than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or less. In some cases, the viscosity is between about 10 and 10,000 centipoise.

A cantharidin formulation can be free of or have a reduced level of Magnesium ions ($Mg^{2-}$) or reagents that can produce magnesium ions. A cantharidin formulation can be free of or have a reduced level of manganese ions ($Mn^{2+}$) or reagents that can produce manganese ions. A cantharidin formulation can be free of or have a reduced level of magnesium and manganese ions or reagents that can produce magnesium and manganese ions. $Mg^{2+}$ and/or $Mn^{2+}$ ions can interact with cantharidin, limiting its activity (e.g., therapeutic efficacy). A cantharidin formulation can comprise about 30, 20, 15, 10, 5, 4, 3, 2, 1, or about 0.1% magnesium ions. A cantharidin formulation can comprise about 30, 20, 15, 10, 5, 4, 3, 2, 1, 0.1% magnesium ions or less. A cantharidin formulation can comprise between about 0.1 and 1% magnesium ions. A cantharidin formulation can comprise less than about 0.1% magnesium ions. A cantharidin formulation can comprise between about 5 and 0.1% magnesium ions. A cantharidin formulation may comprise magnesium ions. A cantharidin formulation may not contain magnesium ions. A cantharidin formulation can be free or have a reduced level of manganese, calcium, sodium and potassium ions for similar reasons. For example, a cantharidin formulation can comprise about 30, 20, 15, 10, 5, 4, 3, 2, 1, or about 0.1% manganese ions. A cantharidin formulation can comprise about 30, 20, 15, 10, 5, 4, 3, 2, 1, 0.1% manganese ions or less. A cantharidin formulation can comprise between about 0.1 and 1% manganese ions. A cantharidin formulation can comprise less than about 0.1% manganese ions. A cantharidin formulation can comprise between about 5 and 0.1% manganese ions. A cantharidin formulation may comprise manganese ions. A cantharidin formulation may not contain manganese ions.

A cantharidin formulation of the present disclosure can contain other topical agents. Topical agents include, but are not limited to, local anesthetics, local analgesics, antimicrobial agents, microbicidal agents, disinfectants, antiseptics, antibiotics, bactericidal agents, bacteriostatic agents, cleansing agents, anti-inflammatory agents, anti-infective agents (e.g., gentian violet), emollients, astringents, anti-acne agents, anti-virals, anti-fungals, fungicides, anti-psoriasis agents, antiparasitics, steroid hormones such as corticosteroids. Examples of topical agents include, but are not limited to, Altabax (retapamulin), Amevive (alefacept), Avita gel, Bactroban cream, benzamycin, erythromycin, botox, cefazolin, dextrose, chloraprep (chlorhexidine gluconate), clindamycin phosphate, condylox (pokofilox), desonate (desonide), differin (adapalene), Dynabac, Elidel, Erivedge (vismodegib), Estrostep, norethindrone acetate, ethinyl estradiol, Extina (ketoconazole), Fiacea (azelaic acid), Finevin, Firazyr (icatibant), Gralise (gabapentin), Horizant (gapabentin enacarbil), hydrochloric acid, hydrogen peroxide, lamin, Invanz, lontocaine, IvyBlock, Klaron (sodium sulfacet amide), Lamisil (terbinafine hydrochloride), LaViv (azficel-T), Lustra, Luxiq (betamethasone valerate), Mentax (butenafine HCl), MetroLotion, Minoxidil, Noritatc, nitric acid, Omnicef, Ortho Tri-Cyclcc, norgcstimatc, Picato (ingcnol mcbutatc), Propecia, Protopic (tacrolimus), Condylox (podophotoxin), Regranex (becaplermin), Renova, tratinoin, salagen, sandalwood oil, salicylic acid, Sklice (ivermectin), Stelara (ustkinumab), Sulfamylon, Sylatron (peg interferon alpha-2b), Tazorac, Teflaro (ceftaroline fosamil), Thalomid, Trichloroacetic acid, Tygacil (tigecycline), Veltin (clindamycin phosphate), tretinoin, Veregen (green tea sincatechins), Verdeso (desonide), Vibativ (telavancin), Vibativ (telavancin), Xyzal (levoctirizine dihydrochloride), Yervoy (ipilimumab), Zelboraf (vemurafenib), and Zyclara (imiquimod).

A cantharidin formulation can have the following components:

TABLE 1

Example cantharidin formulation

| Component | Amount (% weight/volume) |
|---|---|
| Ethanol | 0-99% |
| Acetone | 0-99% |
| Hydroxypropylcellulose | 0-10% |
| Nitrocellulose | 0-10% |
| Castor Oil | 0-5% |
| Camphor | 0-5% |
| Cantharidin | 0.001-7% |
| Denatonium Benzoate | 0.00001-1% |
| Gentian Violet | 0.00001-1% |

TABLE 2

An example of a cantharidin formulation that may be useful in treating heavily keratinized skin

| Component | Amount (% weight/volume) |
|---|---|
| Ethanol | 60.0% |
| Acetone | 13.0% |
| Salicylic Acid | 3.0% |
| Nitrocellulose | 1.0% |
| Castor Oil | 0.5% |
| Camphor | 0.5% |
| Cantharic acid | 1.0% |
| Trichloroacetic acid | 20.0% |
| Sodium lauryl sulfate | 1.0% |

TABLE 3

An example of a DMSO-based cantharidin formulation visible under ultraviolet (UV) light that may be useful in treating cosmetic lesion on the face of a subject

| Component | Amount (% weight/volume) |
|---|---|
| DMSO | 97.4% |
| Nitrocellulose | 1.0% |
| Castor Oil | 0.5% |
| Camphor | 0.5% |
| Cantharidin | 0.5% |
| Mag-indo-1 | 0.1% |

TABLE 4

Example of a very thin simple cantharidin formulation that may be useful in treating larger lesions

| Component | Amount (% weight/volume) |
|---|---|
| Ethanol | 49.25% |
| Acetone | 49.25% |
| Hydroxypropylcellulose | 0.0% |
| Nitrocellulose | 0.5% |
| Castor Oil | 0.0% |
| Camphor | 0.0% |
| Cantharidin | 1.0% |
| Denatonium Benzoate | 0.0% |
| Gentian Violet | 0.0% |

TABLE 5

Example of an easily visualized thick cantharidin formulation that may be useful where adhesion is a priority

| Component | Amount (% weight/volume) |
|---|---|
| Ethanol | 80.0% |
| Acetone | 8.9% |
| Hydroxypropylcellulose | 4.0% |
| Nitrocellulose | 4.0% |
| Castor Oil | 0.5% |
| Camphor | 0.0% |
| Cantharidin | 2.5% |
| Denatonium Benzoate | 0.0% |
| Gentian Violet | 0.1% |

TABLE 6

Example of a quick drying cantharidin formulation that may be useful as a chemical peel

| Component | Amount (% weight/volume) |
|---|---|
| Ethanol | 10.0% |
| Acetone | 89.5% |
| Hydroxypropylcellulose | 0.1% |
| Nitrocellulose | 0.1% |
| Castor Oil | 0.1% |
| Camphor | 0.1% |
| Cantharidin | 0.1% |
| Denatonium Benzoate | 0.0% |
| Gentian Violet | 0.0001% |

TABLE 7

Example of a cantharidin formulation for the treatment of warts and molluscum

| Component | Amount (% weight/volume) |
|---|---|
| Ethanol | 70-90% |
| Acetone | 10-20% |
| Hydroxypropylcellulose | 0.2-4.0% |
| Nitrocellulose | 0.2-4.0% |
| Castor Oil | 0.1-1.0% |
| Camphor | 0.1-1.0% |
| Cantharidin | 0.1-1.0% |
| Denatonium Benzoate | 0.0001-0.1% |
| Gentian Violet | 0.0001-0.1% |

The cantharidin solution described in Table 7 can be prepared in the following manner. Acetone, ethanol and nitrocellulose are added to a glass vial to form a mixture. A polytetrafluoroethylene (PTFE) coated stir bar can be added and the mixture mixed until a homogenous viscous mixture is formed. Castor oil and camphor can be added to the mixture and stirred until homogenous. A 1% denatonium benzoate solution in ethanol can be added to the glass vial. A 1% gentian violet solution in ethanol can be added to the glass vial. Greater than 95% pure Cantharidin powder can be added to the glass vial. The mixture can be mixed until homogeneous. Hydroxypropylcellulose can be added and the mixture mixed until fully gelled and homogenous.

Applicator Devices and Kits

Another aspect of the present disclosure provides applicator devices, systems and kits for treating warts. An applicator device for treating warts or other skin ailments can include a cantharidin formulation of the present disclosure. In some cases, an applicator device for delivering a cantharidin formulation can comprise at least one reservoir or chamber containing the cantharidin formulation, and an application unit in fluid communication with the reservoir to deliver the cantharidin formulation to a subject.

A system for delivering a cantharidin formulation can comprise a cantharidin formulation, and an applicator device configured to deliver the cantharidin formulation. The cantharidin formulation can include excipients. The cantharidin formulation can have any concentration or composition described above or elsewhere herein. In some examples, the cantharidin formulation contains at least about 0.001% (w/v) cantharidin. In some cases, the cantharidin formulation contains at least about 0.01%, 0.1% or 1% cantharidin. As other examples, the cantharidin formulation comprises at least about 5% (w/v) of an excipient.

The applicator device can comprise an applicator unit and one or more reservoirs each comprising one or more cavities in fluid communication with the applicator unit. An individual reservoir can have various shapes. In some examples, a reservoir has a circular, triangular, square, rectangular, pentagonal, or hexagonal cross-section, or any partial shape or combination thereof. In some examples, a reservoir is cylindrical. In some examples, a reservoir is spherical or oval.

A system for delivering a cantharidin formulation to a subject can comprise a reservoir comprising a cavity with the cantharidin formulation. A reservoir can have a volume less than or equal to about 10 mL. A reservoir can be compressible to induce a pressure increase in the reservoir in excess of about 1.0 atm. Alternatively a portion of the reservoir can be compressible (e.g., a plunger or button) to induce flow of the cantharidin solution. A system can include an applicator unit comprising an adaptor and an applicator tip. An applicator tip comprises an opening and a channel in fluid communication with the reservoir. An applicator tip can be configured to transfer the cantharidin formulation from the reservoir to a location external to the applicator tip, such as to an area of the subject (e.g., skin location).

In some cases, the applicator unit comprises a transparent cap that is configured to cover the applicator tip. The transparent cap can be formed of a polymeric material, such as a plastic (e.g., thermoplastic). An application unit can comprise a barrier on the opening. The transparent cap can comprise a puncture apparatus (e.g., needle) that is configured to puncture the barrier.

Figure 8:
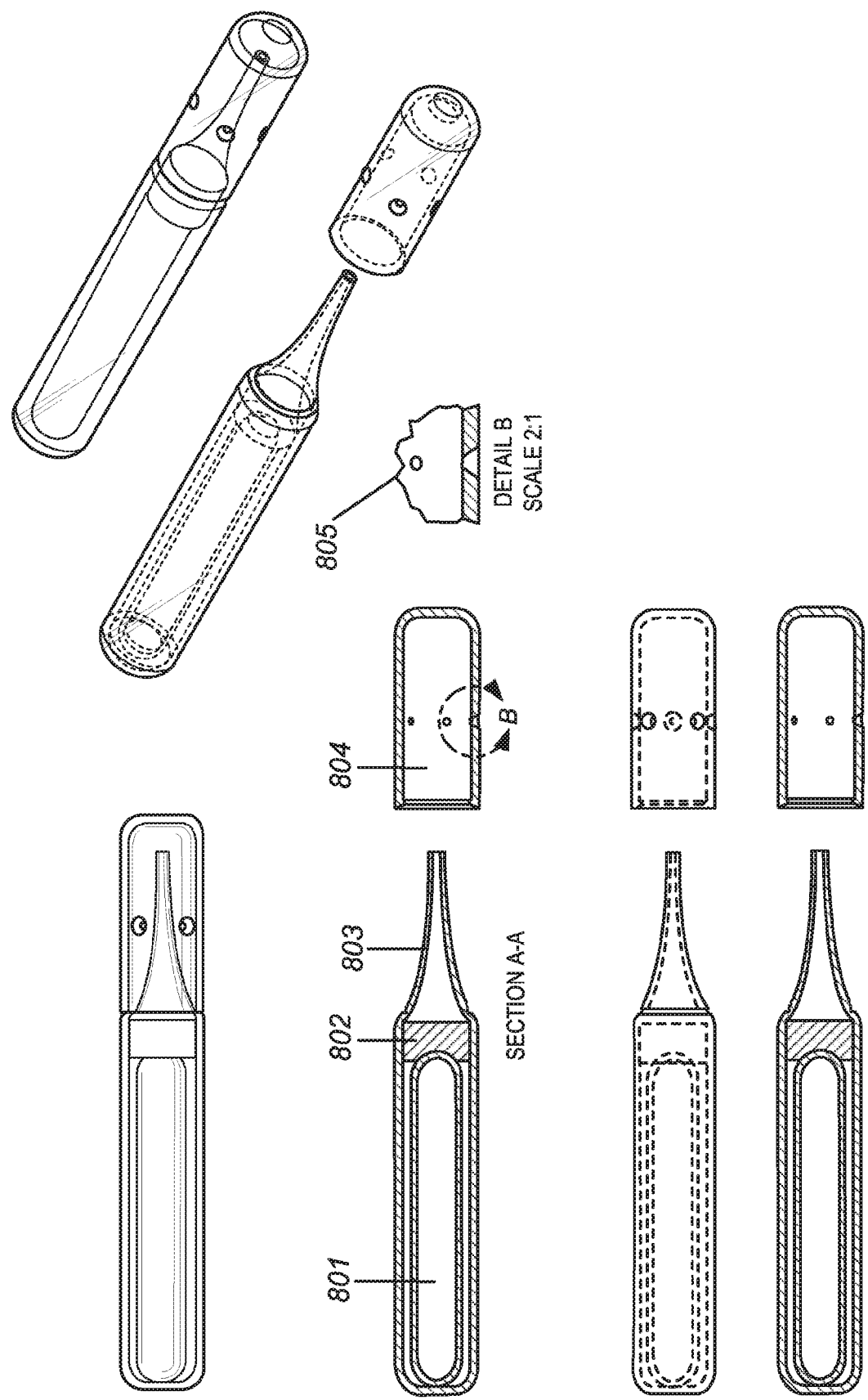
FIG. 8 depicts line drawings and 3D renderings of an applicator device with a vented removable cap, in accordance with some embodiments of the present disclosure.

The transparent cap may be vented. For example, FIG. 8 illustrates an application device with an ampule contained within a plastic reservoir 801 that can be attached to an applicator tip 803 and contain a filter 802. The applicator tip 803 can be enclosed by a removable transparent cap 804 with one or more vents 805. The transparent cap may not be vented. The transparent cap may be vented so that a solvent may leave (e.g., evaporate from) the applicator unit. A portion of the solvent may leave the applicator unit. The entire amount of the solvent may leave the applicator unit. The transparent cap may be vented so that a liquid drug product is retained within the applicator unit. The transparent cap may be vented so that liquid drug product may be retained but solvent may leave. In cases where all or partial amounts of the solvent leave the applicator unit, the liquid drug product may completely or partially solidify. The liquid drug product may completely solidify. The liquid drug product may partially solidify. A solvent with a high vapor pressure may be used in the described formulations. In such cases, the solvent may readily vaporize under ambient conditions. A solvent may not have a high vapor pressure. Solvents with high vapor pressures may quickly leave (e.g., evaporate from) vented applicator units. In some cases, when a liquid drug product solidifies it may not be reused.

In some cases, the adaptor locks into the screw cap of the reservoir. The adaptor can lock into the screw cap using a locking mechanism, such as, for example, two flexible prongs that lock into an indentation.

The opening of the applicator tip can have a diameter less than or equal to about 20 millimeters (mm), 18 mm, 16 mm, 14 mm, 12 mm, 10 mm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, or 0.1 mm. In some situations, the size of the opening is adjustable to regulate the flow rate of the cantharidin formulation out of the applicator tip.

A system can comprise a cantharidin formulation. In some non-limiting examples, the cantharidin formulation can contain at least about 0.001% (w/v) cantharidin. In some cases, the cantharidin formulation can contain at least about 0.01%, 0.1% or 1% cantharidin. In some non-limiting examples, the cantharidin formulation can contain greater than or equal to 5% (w/v) of excipients. In other non-limiting examples, the cantharidin formulation can comprise less than or equal to 1% (w/v) cantharidin, cantharidic acid, norcantharidin or palasonin combined.

In some non-limiting examples, the reservoir can have a volume less than or equal to about 50 mL, 40 mL, 30 mL, 20 mL, 10 mL, 5 mL, 1 mL, 0.5 mL, or 0.1 mL. In some non-limiting examples, the reservoir can have a screw cap or snap (or snap-on) cap on or already attached cap at one end. The cap can include ribs that enable the cap to be releasably secured to the reservoir. The cap can seal the reservoir. In some situations, the seal is a hermetic seal.

The applicator can contain a glass ampule that holds the cantharidin formulation. The glass ampule can be adapted to be broken or punctured to release the cantharidin formulation. In some cases, the glass ampule can be punctured into several pieces. In some cases, an outer plastic reservoir can be compressed to shatter the glass ampule releasing the cantharidin formulation. In some examples, an ampule is made of USP type I borosilicate glass, USP type II borosilicate glass, or USP type III borosilicate glass. As an alternative, the applicator can comprise an ampule formed of a polymeric material, such as plastic or rubber. The ampule in such a case may be punctured or shattered to release the cantharidin formulation.

The applicator unit may have a filter. The applicator unit may have more than one filter. The applicator unit may not have a filter. The filter may filter out aggregates, particles, pieces of material or the like. These aggregates, particles, or piece of materials may be but are not limited to glass particles, plastic particles, precipitates from the liquid drug formulation or other aggregates. One or more filters may be included in the applicator unit to remove aggregates, particles, or pieces of material prior to applying the liquid drug formulation to the skin. One or more filters may be included in the applicator unit to provide a barrier. One or more filters may provide a barrier that may block delivery of additional drug product. One or more filters may provide a barrier to block additional delivery of solidified drug product. A filter can made of plastic with one or more holes or alternatively can be a mesh material (e.g., polyester or polyethylene).

In some cases, a system for delivering a cantharidin formulation can comprise a cantharidin formulation and an applicator device. In some non-limiting examples, the cantharidin formulation can comprise an excipient and the applicator device can be configured to deliver the cantharidin formulation. In some non-limiting examples, the cantharidin formulation can comprise at least about 0.001% (w/v) cantharidin. In some non-limiting examples, the cantharidin formulation can comprise greater than or equal to 5% (w/v) of an excipient.

In some cases, the applicator device can comprise an applicator unit and one or more reservoirs each comprising one or more cavities in fluid communication with the applicator unit. In some non-limiting examples, the reservoir can comprise a screw cap on one end. In some non-limiting examples, the reservoir can have a volume less than or equal to 5 mL. In some non-limiting examples, the reservoir can be compressible to induce a pressure increase in the reservoir in excess of about 1.0 atm. In some non-limiting examples, the applicator unit can comprise an applicator tip that comprises an opening and an inner-channel in fluid communication with the reservoir. In some non-limiting examples, the applicator tip can be configured to transfer the cantharidin formulation from the reservoir to a location external to the applicator tip.

FIG. 1A illustrates an example of a reservoir that can hold a cantharidin formulation. The reservoir 101 can be equipped with a locking mechanism 102 that can be attached to other modules, such as the applicator unit depicted in FIG. 2. The upper portion of the reservoir 101 can have a hollow screw cap 103. Alternatively, the upper portion of the reservoir 101 can have a different kind of cap or no cap at all. The hollow screw cap can be further equipped with a barrier 104. Alternatively, the hollow screw cap can have no barrier. The barrier 104 can be a foil barrier. Alternatively, the barrier 104 can be made of other materials, such as natural polymers, synthetic polymers, and metals. The barrier 104 can keep the contents of the reservoir sterile. The barrier 104 can keep the contents within the reservoir. The barrier 104 can also have other practical functions.

The reservoir can be compressible or include a pressure applicator member (e.g., plunger or button) to induce a pressure increase inside the reservoir in excess of about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm. or 40 atm. The reservoir can be compressible to induce a pressure increase inside the reservoir greater than or equal to about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm. or 40 atm. In some cases, the pressure in the reservoir is increased by a factor of at most about 100 atm, 50 atm, 40 atm, 30 atm, 20 atm, 10 atm or 5 atm. In some examples, the reservoir is compressible to induce a pressure increase in the reservoir from about 1 atm to 20 atm, 1 atm to 15 atm, 1 atm to 10 atm, or 1 atm to 5 atm.

In some cases, the reservoir can be compressible or include a pressure applicator member to induce a pressure inside the reservoir that is greater than about 1.0 atm, 1.1 atm, 1.2 atm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm. or 40 atm. The reservoir can be compressible to induce a pressure inside the reservoir that is greater than or equal to about 1.0 atm, 1.1 atm, 1.2 arm, 1.3 atm, 1.4 atm, 1.5 atm, 1.6 atm, 1.7 atm, 1.8 atm, 1.9 atm, 2.0 atm, 3.0 atm, 4.0 atm, 5.0 atm, 6.0 atm, 7.0 atm, 8.0 atm, 9.0 atm, 10 atm, 20 atm, 30 atm. or 40 atm. In some cases, the pressure in the reservoir is increased to at most about 100 atm, 50 atm, 40 atm, 30 atm, 20 atm, 10 atm or 5 atm. In some examples, the reservoir is compressible to induce a pressure in the reservoir from about 1 atm to 20 atm, 1 atm to 15 atm, 1 atm to 10 atm, or 1 atm to 5 atm.

Alternatively, the device can contain a wicking material (e.g., polyester fibers) that can allow for the movement of the cantharidin solution from the end of the reservoir to the applicator tip.

Alternatively, the device can have a lever or rotating arm, which physically moves a pre-set amount of cantharidin solution out of the applicator tip when a button is pushed or a trigger is pulled or a dial is turned.

Figure 1B:
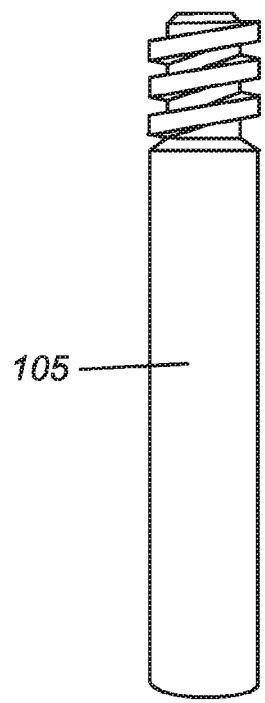

FIG. 1B illustrates another example of a reservoir. The reservoir 105 can have a substantially different shape from reservoir 101. The reservoir 105 can have a substantially different size from reservoir 101.

The reservoir can have a volume from about 0.1 mL to 100 mL, or about 0.1 mL to 50 mL, or about 1 mL to 20 mL, or about 0.1 mL to 10 mL, or about 0.5 to 5 mL, or about 0.5 mL to 3 mL. The reservoir can have a volume less than or equal to about 100 mL, about 50 mL, about 10 mL, about 5 mL, about 3 mL, about 1 mL, about 0.5 mL, or about 0.1 mL.

The reservoir can have a shape that is mainly or substantially cylindrical or spherical. Alternatively, the reservoir can have a shape that is mainly or substantially rectangular. The reservoir can have 1 edge. Alternatively, the reservoir can have 2 or more edges. Further, the reservoir can have an irregular shape.

The reservoir can be at least partially or wholly formed of a polymeric material (e.g., plastic). The plastic used can be but is not limited to polypropanol, low-density polyethylene, medium-density polyethylene, high-density polyethylene, or polytetrafluoroethylene or some combination thereof. As an alternative, the reservoir can be at least partially or wholly formed of a metallic material (e.g., stainless steel or aluminum). In an example, a portion of the reservoir is formed of a polymeric material, and a remainder of the reservoir is formed of a metallic material.

The reservoir can be at least partially or wholly formed of a polymeric material (e.g., plastic). As an alternative, the reservoir can be at least partially or wholly formed of a metallic material (e.g., stainless steel or aluminum). In an example, a portion of the reservoir is formed of a polymeric material, and a remainder of the reservoir is formed of a metallic material.

Reservoirs of the present invention can comprise any of the elements, alone or in combination, and/or properties described above or elsewhere herein.

Figure 2A:
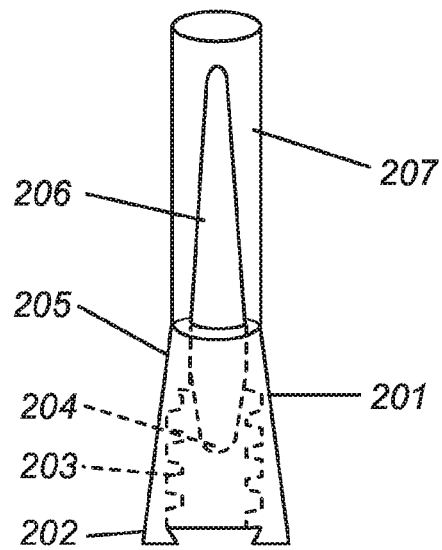
FIGS. 2A-2C schematically illustrate an applicator unit, in accordance with some embodiments of the present disclosure.

FIG. 2A illustrates an example of an applicator unit that can be used to deliver cantharidin formulation. The applicator unit 201 can be used to deliver and/or apply the cantharidin formulation. The applicator unit 201 can be equipped with a locking mechanism 202 that can be attached to other modules, such as the reservoir depicted in FIG. 1. Alternatively, the applicator unit 201 can have no locking mechanism. The applicator unit 201 can have a hollow screw cap 203. The hollow screw cap 203 can be screwed onto a complementary hollow screw cap, such as the one in the reservoir depicted in FIG. 1A. Alternatively, the applicator unit 201 can have a different kind of cap or no cap at all. The applicator unit 201 can have a barrier breaker 204, which can puncture a barrier once the applicator unit is attached to the reservoir. The barrier can be the foil barrier in the reservoir depicted in FIG. 1A. Alternatively, the applicator unit can have no barrier breaker. The applicator unit can have a seal 205, which can keep the cantharidin formulation within the reservoir once the applicator unit is attached to the reservoir. The reservoir containing the cantharidin formulation can be the reservoir depicted in FIG. 1A. Alternatively, the applicator unit can have no seal. The applicator unit 201 can have a hollow applicator tip 206. When the reservoir is attached to the applicator unit, the cantharidin formulation can flow through the hollow applicator tip. Further, the hollow applicator tip can direct the application of the cantharidin formulation. The applicator unit 201 can have a removable cap 207. The removable cap 207 can be transparent. The removable cap 207 can contain solution that leaks out. The removable cap 207 can allow for visualization of the solution prior to application of the cantharidin formulation. The removable cap 207 can allow for proper disposal. Alternatively, the applicator unit can have no removable cap.

Figure 2B:
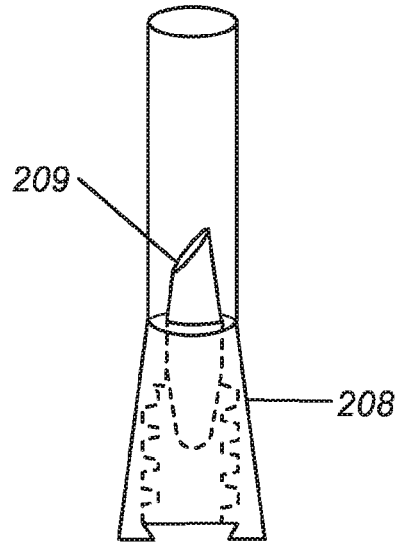

FIG. 2B illustrates another example of an applicator unit that can be used to deliver a cantharidin formulation. The applicator unit 208 can have a porous applicator tip 209. The porous applicator tip 209 can allow for the precise application of the cantharidin solution.

Figure 2C:
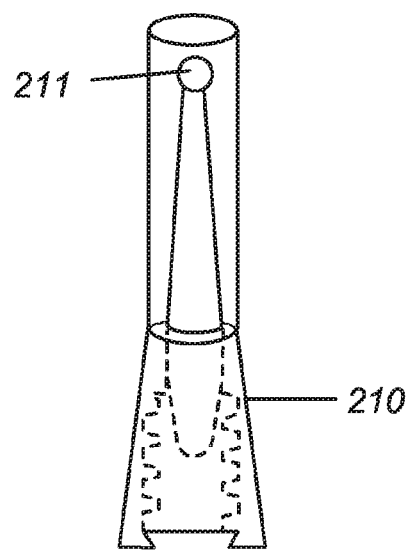

FIG. 2C illustrates yet another example of an applicator unit. The applicator unit 210 can have a hollow applicator tip 211 with a porous end. The hollow applicator tip 211 with a porous end can allow for the precise application of the cantharidin solution.

Figure 7A:
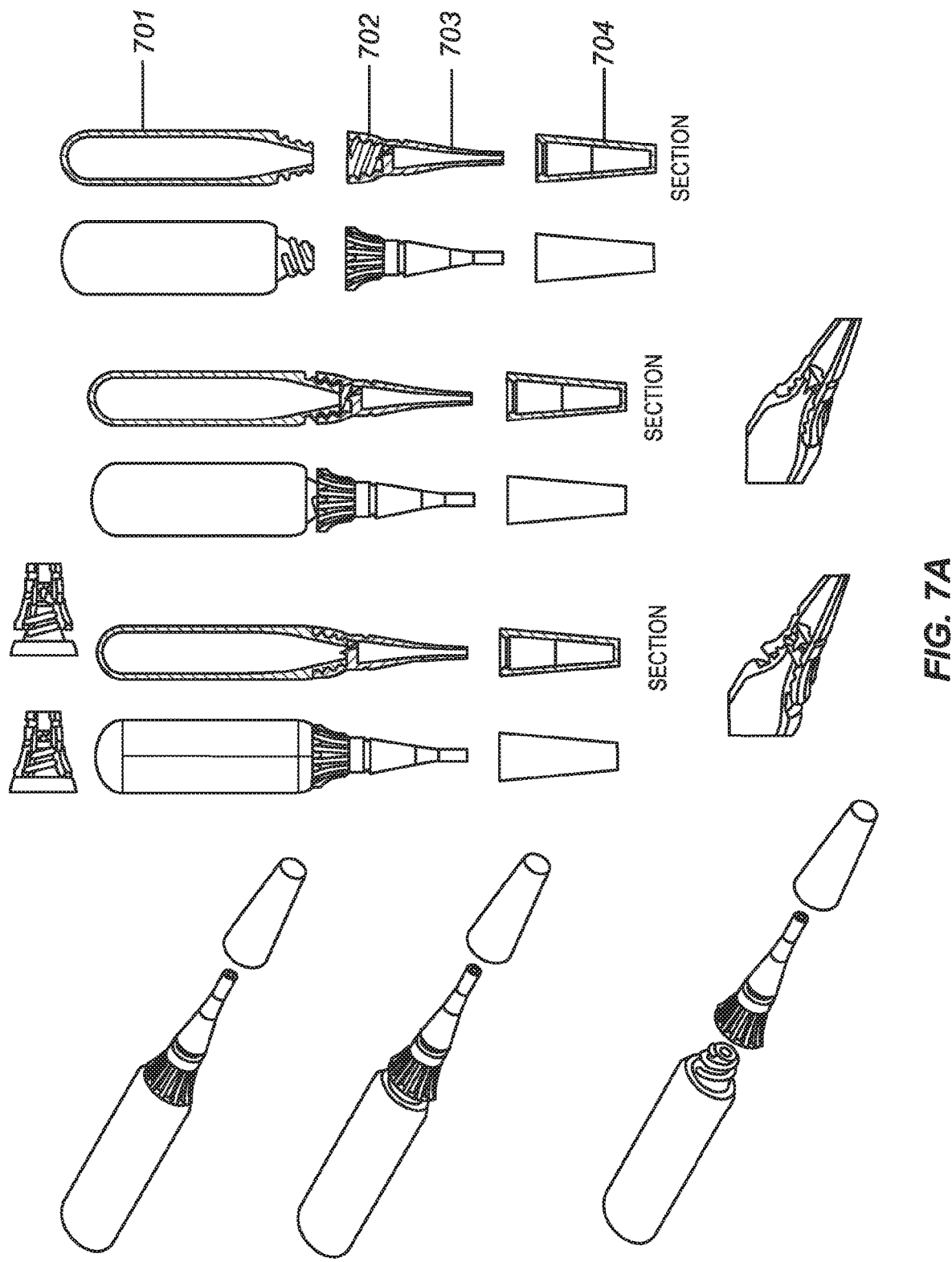
FIGS. 7A-7B depict line drawings (FIG. 7A) and 3D renderings (FIG. 7B) of an applicator device, in accordance with some embodiments of the present disclosure.
Figure 7B:
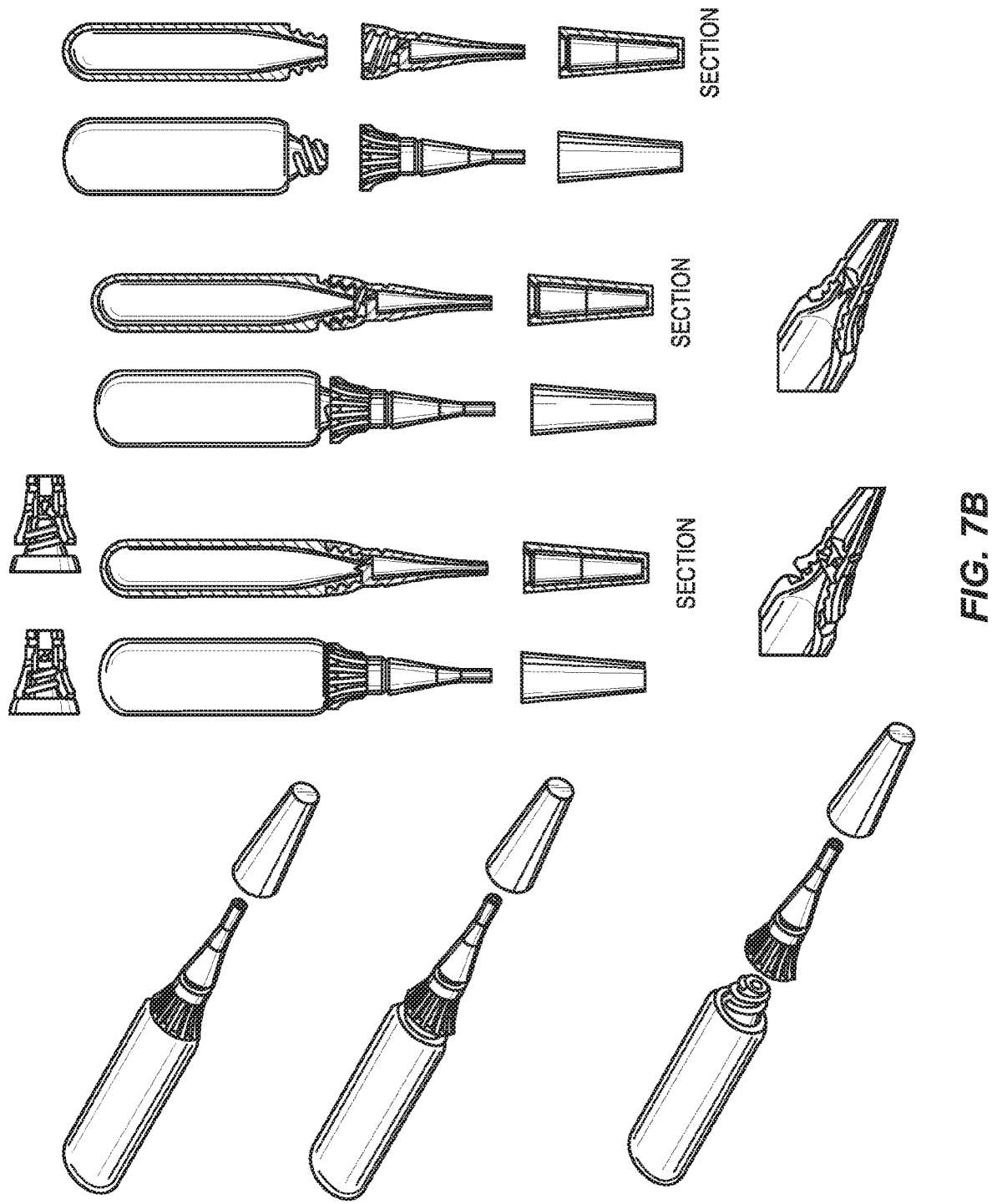

FIGS. 7A and 7B illustrate several examples of an applicator unit. The applicator unit can have a reservoir 701 that may be attached to an applicator tip 703 (e.g., hollow, porous, or hollow with a porous end) by a hollow screw cap 702. The applicator tip can be enclosed by a removable cap 704.

The applicator tip can have a length from about 0.1 centimeters (cm) to 10 cm, or from about 0.1 cm to 5 cm, or from about 0.5 cm to 5 cm, or from about 0.5 cm to 3 cm, or from about 1 cm to 3 cm, or from about 1 cm to 2 cm.

The applicator tip can comprise a channel. The channel can be a hollow inner channel. The channel can be in fluid communication with the reservoir. The cantharidin formulation can flow through the channel.

The applicator tip can comprise an opening. The opening can have a shape that is circular, triangular, square, rectangular, pentagonal or hexagonal, or any partial shape or combination thereof. In an example, the opening is circular. The opening can be in fluid communication with the channel, which can be in fluid communication with a reservoir (or chamber) having the cantharidin formulation. The cantharidin formulation can flow through the opening. The applicator tip can be soft or rough. The applicator tip can be used to gently apply the cantharidin formulation to the skin to limit penetration or to abrade the skin during delivery to enhance penetration into the skin.

An opening can have a diameter from about 0.1 mm to 20 mm, about 0.1 mm to 10 mm, about 0.1 mm to 5 mm, about 0.5 mm to 5 mm, or about 0.5 mm to 3 mm. The opening can have a diameter less than or equal to about 20 mm, about 10 mm, about 5 mm, about 1 mm, about 0.5 mm, or about 0.1 mm.

Applicator units of the present disclosure can comprise any of the elements, alone or in combination, and/or properties described above or elsewhere herein.

Figure 3:
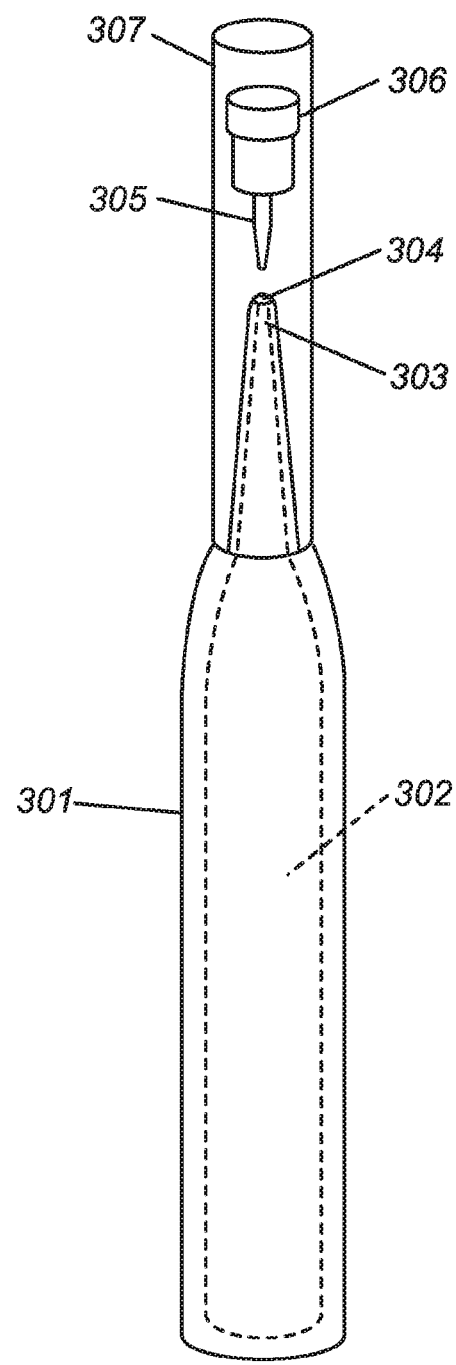
FIG. 3 depicts an applicator device, in accordance with some embodiments of the present disclosure.

FIG. 3 illustrates an example of an applicator device that can be used to deliver a cantharidin formulation to a subject. The application device 301 can be used to deliver the cantharidin formulation. The applicator device 301 can have a reservoir 302 and an applicator unit 303. The reservoir 302 can contain cantharidin formulation. The applicator unit 303 can have an applicator tip 304. Pressure can be exerted to reservoir 302 to induce flow of the cantharidin formulation to the applicator unit 303. The cantharidin formulation can be applied and/or delivered through the applicator tip 304.

The applicator tip 304 can be a sealed hollow tip. The sealed hollow tip can be punctured by a seal piercing mechanism 305. The seal piercing mechanism 305 can be lined up with the sealed hollow tip. A grip 306 can be pressed down to apply pressure to the seal piercing mechanism 305 and puncture the seal on applicator tip 304.

The applicator device 301 can have a removable cap 307. The removable cap 307 can be transparent. The removable cap 307 can contain solution that leaks out of the applicator device 301. The removable cap 307 can allow for visualization of the solution. The removable cap 307 can allow for proper disposal. The removable cap 307 can be attached to seal piercing mechanism 305. Alternatively, the removable cap 307 can be not attached to seal piercing mechanism 305.

Applicator devices of the present disclosure can comprise any of the elements, alone or in combination, and/or properties described above or elsewhere herein.

Figure 4A:
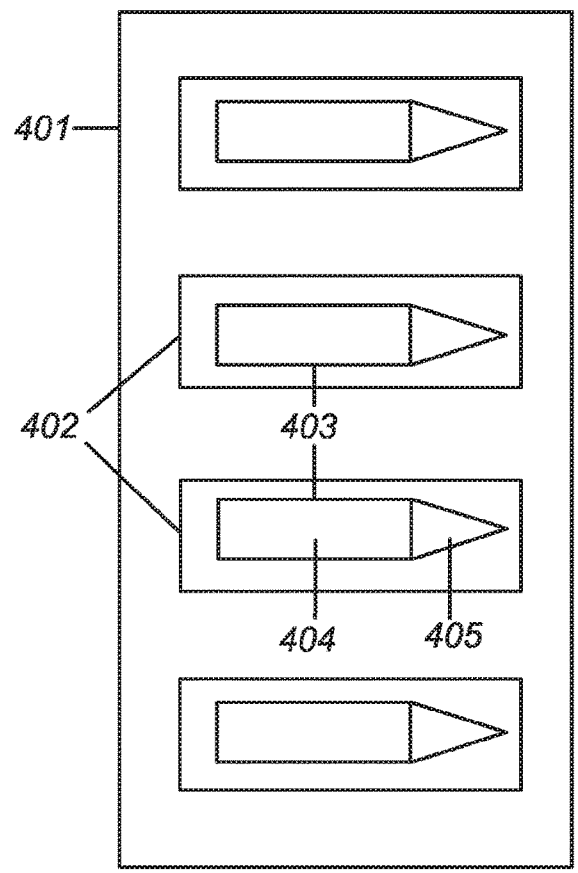
FIGS. 4A-4B depict a kit, in accordance with some embodiments of the present disclosure.

FIG. 4A illustrates an example of a kit for administering cantharidin formulation to a subject. The subject can have an epithelial wart. The kit 401 can comprise of one or more packaging units 402. The packaging units 402 can be separately packaged. The packaging units 402 can be individually removable.

Each packaging unit 402 can comprise an applicator device 403. The applicator device can comprise a reservoir 404 and an applicator unit 405. The reservoir 404 can contain a cantharidin formulation.

Figure 4B:
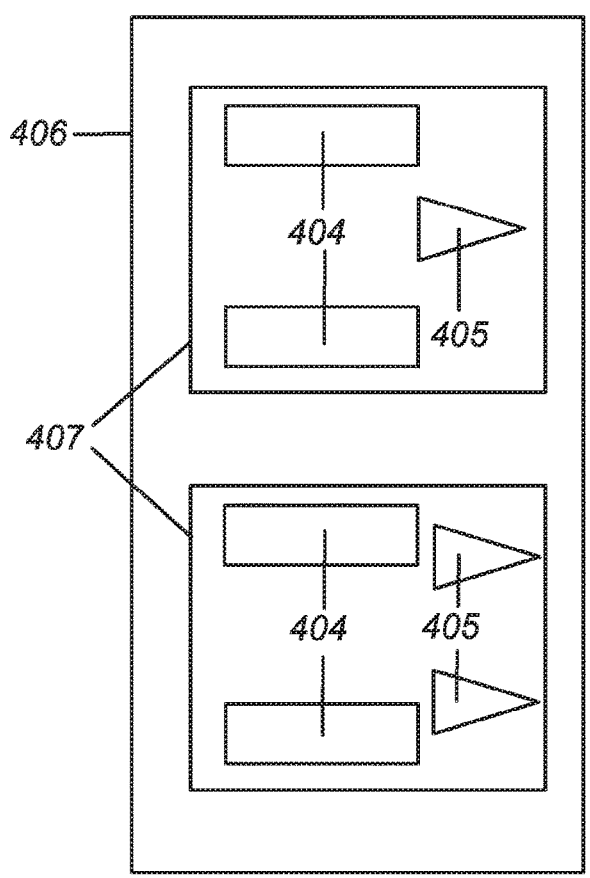
Figure 6A:
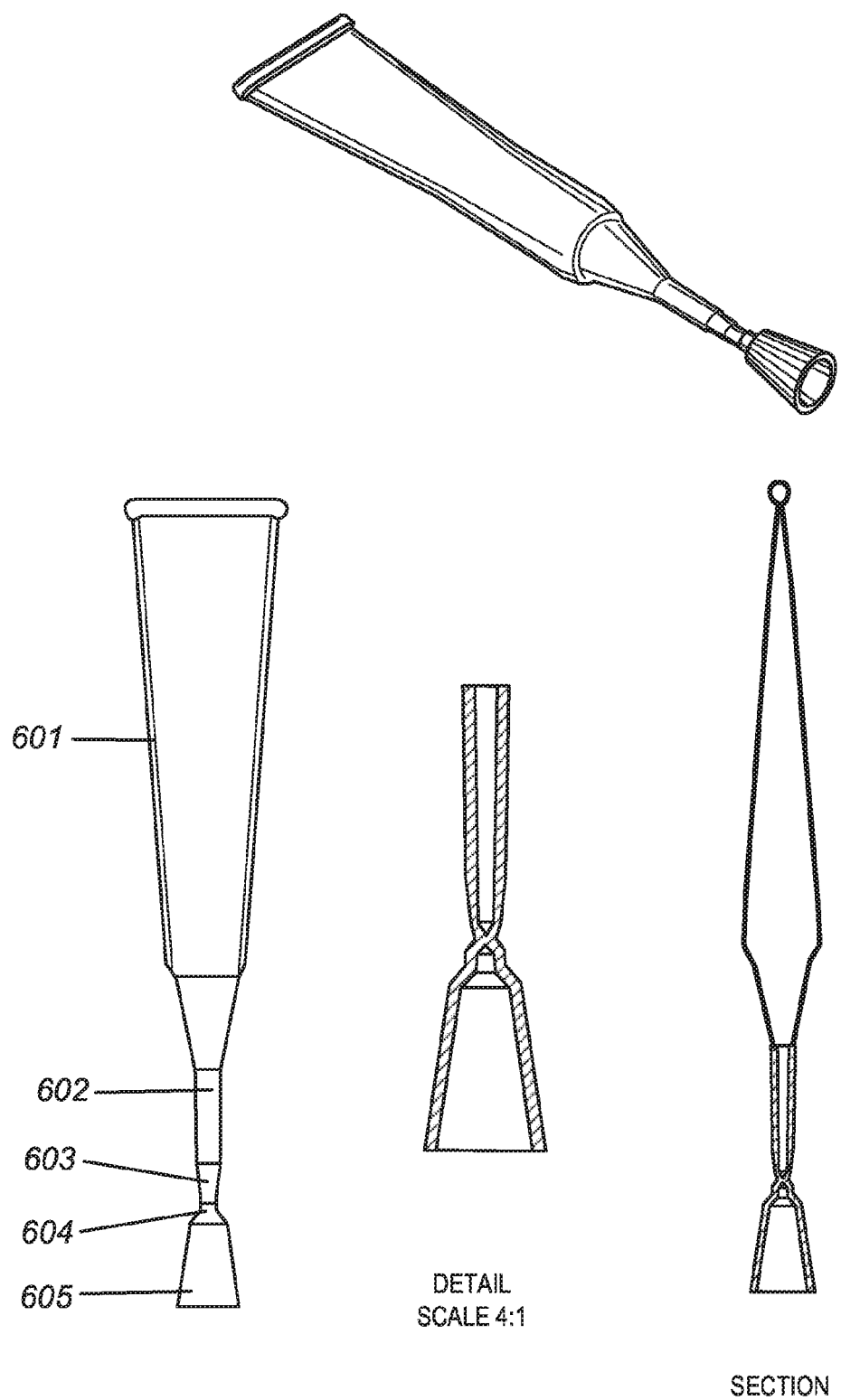
FIGS. 6A-6D depict line drawings (FIG. 6A, 6C) and three-dimensional (3D) renderings (FIG. 6B, 6D) of an applicator device wherein an applicator unit is connected to (FIG. 6A-6B) or separated from (FIG. 6C-6D) a sealing mechanism, in accordance with some embodiments of the present disclosure.
Figure 6B:
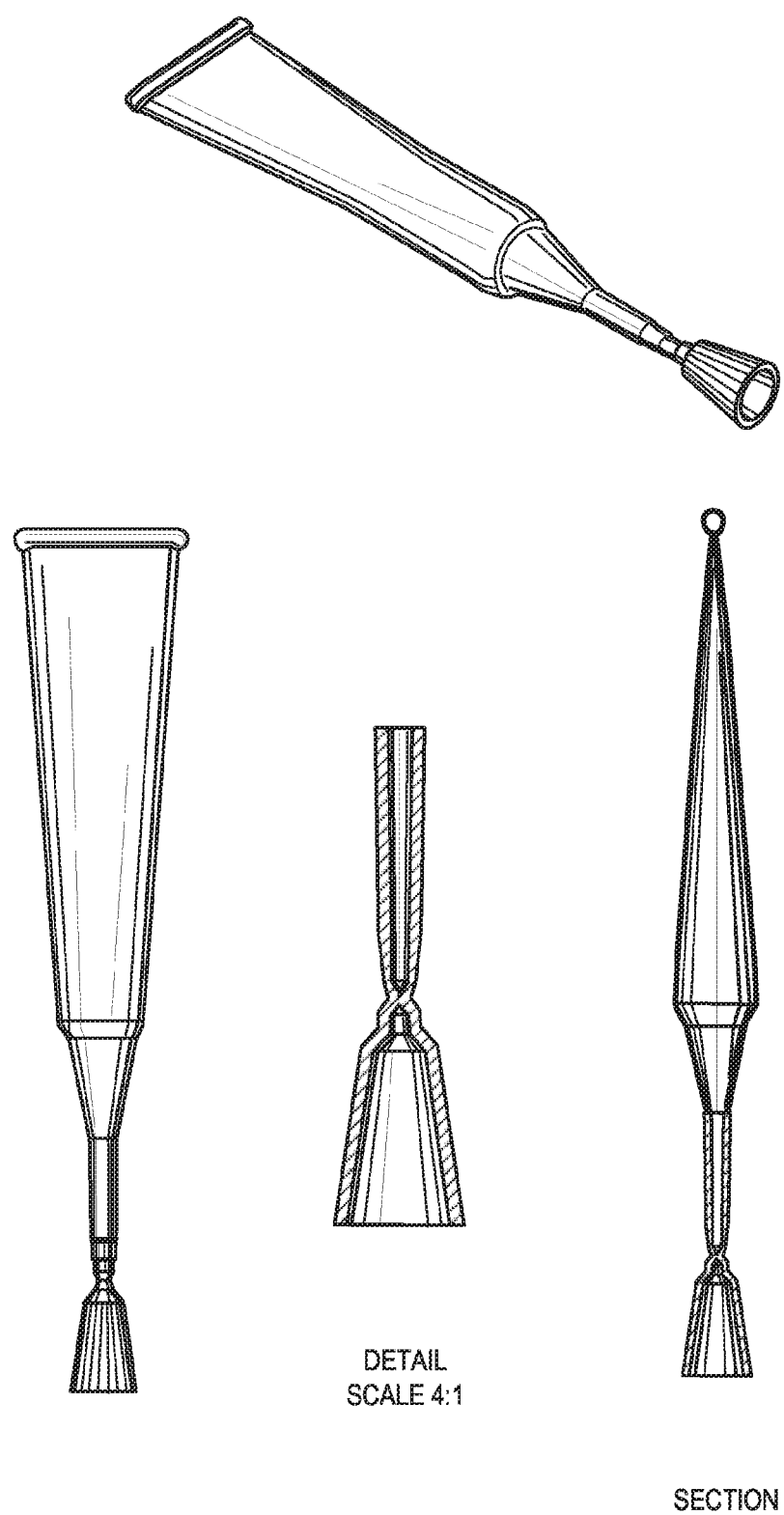
Figure 6C:
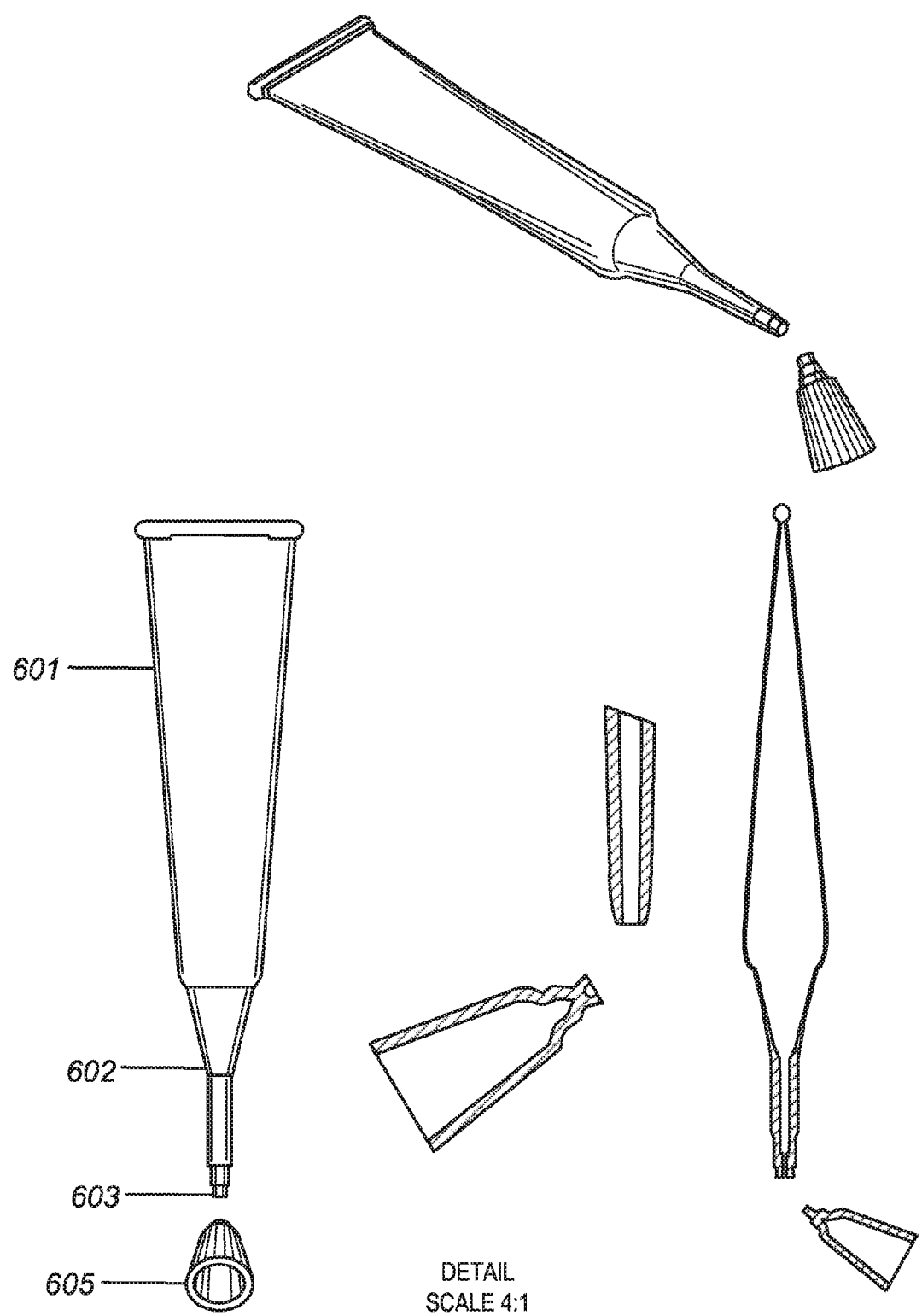
Figure 6D:
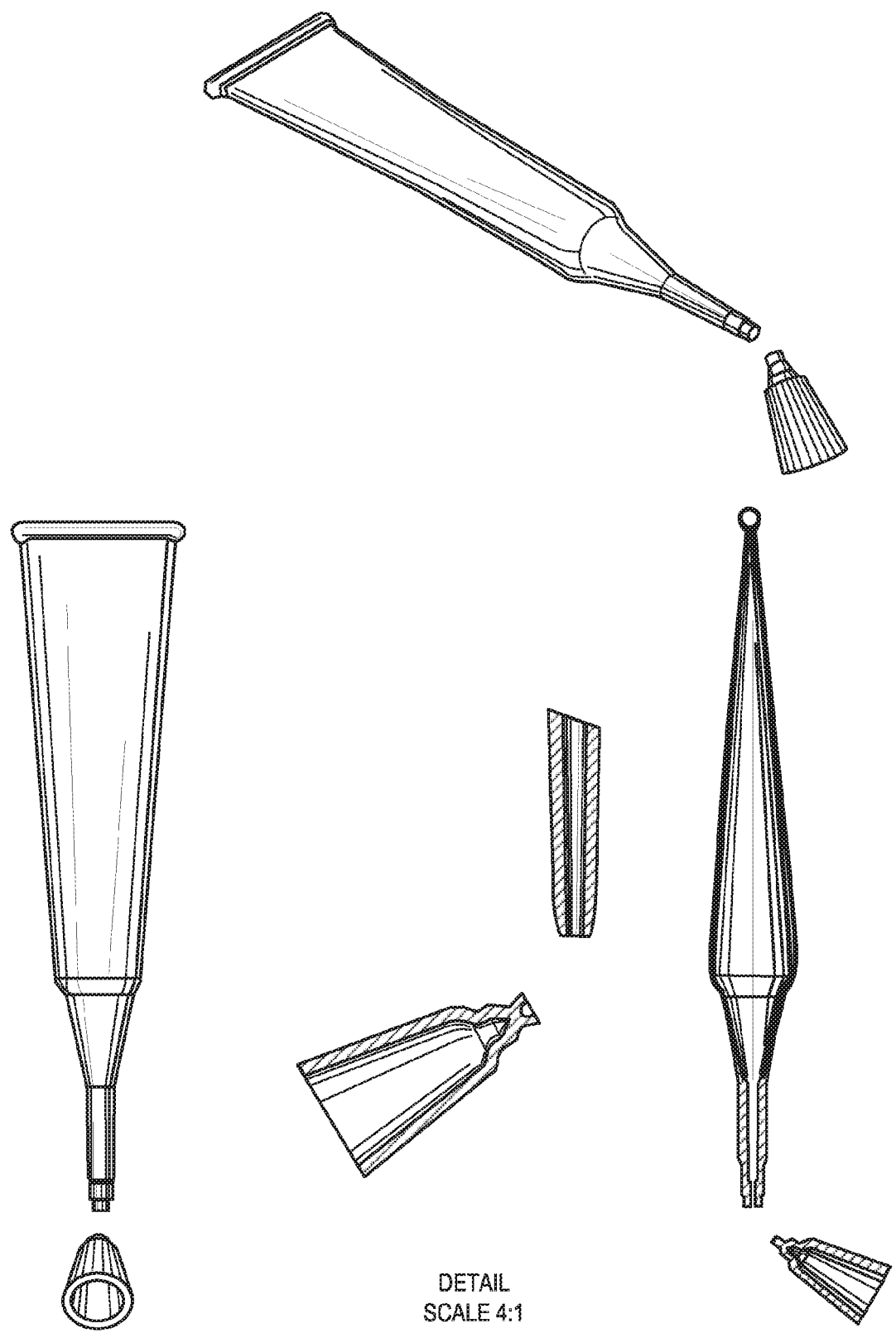

FIG. 4B illustrates another example of a kit. The kit 406 can comprise of one or more packaging units 407. Each packaging unit 407 can comprise a plurality of reservoirs 404 and one or more applicator units 405. The reservoir 404 can contain cantharidin formulation.

Each packaging unit 402 can comprise a plurality of reservoirs 404 and one applicator unit 405. Each packaging unit can contain one dosage unit of the cantharidin formulation. Each packaging unit can contain two dosage units of the cantharidin formulation. Each packaging unit can contain three dosage units of the cantharidin formulation. Each packaging unit can contain four dosage units of the cantharidin formulation. Each packaging unit can contain five dosage units of the cantharidin formulation. Each packaging unit can contain six dosage units of the cantharidin formulation. Each packaging unit can contain six or more dosage units of the cantharidin formulation.

In some cases, the dosage units in each packaging unit can comprise cantharidin in an amount from about 0.1 mL to 100 mL, 0.1 mL to 50 mL, 0.1 mL to 10 mL, or 0.5 mL to 5 mL. In some examples, the dosage units in each packaging unit can comprise cantharidin in an amount less than or equal to about 100 mL, 50 mL, 10 mL, 5 mL, 3 mL, 1 mL, 0.5 mL, or 0.1 mL.

The cantharidin formulation in each packaging unit can comprise at least about 50% (w/v), about 10% (w/v), about 5% (w/v), about 1% (w/v), about 0.5% (w/v), about 0.1% (w/v), about 0.01% or about 0.001% (w/v) of cantharidin.

A kit can comprise one packaging unit. Alternatively, a kit can comprise at least 2, 3, 4, 5, 6, 7, 8, 9, 10, 12, 14, 16, 18, 20, 30, 40, 50, 60, 80, 100, or 200 packaging units.

After a dosage unit of cantharidin formulation is delivered to the subject, an epithelial wart or cutaneous lesion can be removed from the subject within 1, 2, 3, 4, 5, 6, 7, 8, 9, 10, 11, 12, 13, or 14 days. After a dosage unit of cantharidin formulation is delivered to the subject, an epithelial wart or cutaneous lesion can be removed from the subject within 1, 2, 3, 4, 5 or 6 weeks. After a dosage unit of cantharidin formulation is delivered to the subject, an epithelial wart or cutaneous lesion can be removed from the subject within 1, 2 or 3 months.

Kits of the present disclosure can comprise any of the elements, alone or in combination, and/or properties described above or elsewhere herein.

Kits provided herein can include instructional material. The instructional material can include directions that enable a user to apply cantharidin formulations, devices and systems of the present disclosure. The instruction material can include graphical and/or textual information that can direct a subject to administer a cantharidin formulation. The instructional material can provide for an optimal treatment schedule. The instructional material can include different doses of cantharidin, the preparation of the skin of the subject that is to be treated with the cantharidin formulation, the frequency and quantity applied to the skin, how the skin is cared for before and/or after application, and the amount of time cantharidin is left in contact with the skin. The instructional material can allow for the optimally effective treatment of both warts, *Molluscum* or other cutaneous lesion with a cantharidin formulation. In some examples, the instructional material is provided on a user interface (e.g., graphical user interface) of an electronic device of the subject.

FIG. 6 illustrates another example of an applicator device that can be used to deliver a cantharidin formulation of the present disclosure to a subject. The application device can have a reservoir 601 and an applicator unit 602. The reservoir 601 can contain a cantharidin formulation. The applicator unit 602 can have an applicator tip 603 that is connected to a scaling mechanism 604 with a grip 605 (FIG. 6A-6B). Pressure to the grip 605 can break the sealing mechanism 604 (FIG. 6C-6I)). In some cases, pressure to the grip either in one direction perpendicular 605 to the applicator tip 603 or in a twisting motion 605 that is perpendicular to the applicator tip can break the sealing mechanism 604 allowing the cantharidin formulation to be released.

Methods for Treating Subjects

Another aspect of the present disclosure provides methods for delivering cantharidin formulations to subjects, which can be used to treat skin conditions, ailments and/or diseases, such as warts or cutaneous lesions. A method for treating a subject can comprise using an applicator device, system or kit of the disclosure to deliver a cantharidin formulation to a subject having or suspected of having a skin condition, ailment or disease, such as a wart.

Methods of the present disclosure include a user delivering a cantharidin formulation to a subject, or the subject delivering the cantharidin formulation to her or himself.

The applicator device can comprise of a reservoir and an applicator unit. The reservoir can comprise the cantharidin formulation. The applicator unit can be in fluid communication with the reservoir.

The subject can be diagnosed with a skin disease. The skin disease can cause an epithelial wart or other cutaneous lesion. The applicator device can be used to deliver the cantharidin formulations to the epithelial wart or cutaneous lesion. The delivery of the cantharidin formulation can remove the epithelial wart or cutaneous lesion from the subject.

FIGS. 5A-5C illustrate an example of a method for treating a subject with a wart or suspected of having a wart. In FIG. 5A, the subject 501 has or is suspected of having a wart 502 that can be treated by administering a cantharidin formulation. In FIG. 5B, an applicator device 503 comprising a reservoir 504 and an applicator unit 505 is used to deliver a cantharidin formulation to the subject 501. The reservoir 504 can contain a cantharidin formulation. The cantharidin formulation can be administered to the wart 502. The administration of the cantharidin formulation can remove the wart 502 from the subject 501, as shown in FIG. 5C.

The applicator device 503 can be operated by the subject or another individual such as a healthcare provider. In some cases, the applicator device 503 is brought in contact with or proximity to the wart 502 and used to deliver the cantharidin formulation to the wart 502 or an area of the skin adjacent to the wart.

After the cantharidin formulation is delivered to the subject, the epithelial wart can be removed from the subject within 1, 2, 3, 4, 5.6, 7, 8, 9, 10, 11, 12, 13, or 14 days, weeks or months. The cantharidin formulation can be delivered to the subject at least 1, 2, 3, 4, 5, 6, 7, 8, 9, or 10 times a day, week or month.

The amount of cantharidin delivered to the subject in a single administration can be between about 0.001 mg to 100 mg, about 0.1 mg to 50 mg, about 0.1 mg to 10 mg, about 0.5 mg to 10 mg, about 0.5 mg to 5 mg, about 1 mg to 5 mg, or about 1 mg to 2 mg.

The cantharidin formulation delivered to the subject can comprise at least about 0.001% (weight/volume), 0.005%, 0.01%, 0.05%, 0.1%, 0.5%, 1%, 2%, 3%, 4%, 5%, 10%, 20%, 30%, 40%, or 50% of cantharidin. In some cases, the cantharidin formulation delivered to the subject comprises at most about 50% (w/v), 40%, 30%, 20%, or 10%, or 1% of cantharidin.

The cantharidin formulation delivered to the subject can comprise greater than or equal to about 50% (w/v), about 20% (w/v), about 10% (w/v), about 5% (w/v), about 1% (w/v), about 0.5% (w/v), or about 0.1% (w/v) of excipients.

A delivery device or system can be used to deliver a cantharidin formulation to a subject at a dose up to an including about 0.001 mg/day, 0.01 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 mg/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 mg/day, 16 mg/day, 17 mg/day, 18 mg/day, 19 mg/day, or 20 mg/day. As an alternative, a delivery device or system can be used to deliver a cantharidin formulation to a subject at a dose of at least about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 mg/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 mg/day, 16 mg/day, 17 mg/day, 18 mg/day, 19 mg/day, or 20 mg/day.

A delivery device or system of the present disclosure can be used to deliver a cantharidin formulation to a subject (e.g., to a skin area of the subject having or suspected of having a wart or cutaneous lesion) from once a day to once a month or more. As an alternative or in addition to, a delivery device or system of the present disclosure can be used to deliver a cantharidin formulation to a subject from once a day to once a week. As an alternative or in addition to, a delivery device or system of the present disclosure can be used to deliver a cantharidin formulation to a subject at least once a day, once every two days, once every three days, once every four days, once every five days, once every six days, once a week, once every 10 days, once every two weeks, once every three weeks, once a month, once every two months, once every three months, once every four months, once every five months, once every six months, once a year, or more. As an alternative or in addition to, a delivery device or system of the present disclosure can be used to deliver a cantharidin formulation to a subject at least once a day, or twice a day, or three times per day, or four times per day, or five times per day, or six times per day, or seven times per day, or eight times per day, or nine times per day, or ten times per day, or eleven times per day, or twelve times per day, or thirteen times per day, or fourteen times per day, or fifteen times per day, or sixteen times per day, or seventeen times per day, or eighteen times per day, or nineteen times per day, or twenty times per day, or twenty one times per day, or twenty two times per day, or twenty three times per day, or twenty four times per day. As an alternative or in addition to, a delivery device or system of the present disclosure can be used to deliver a cantharidin formulation to a subject as soon as skin begins to epithelialize after previous treatment. As an alternative or in addition to, a delivery device or system of the present disclosure can be used to deliver a cantharidin formulation to a subject as soon as skin has partially epithelized after previous treatment. As an alternative or in addition to, a delivery device or system of the present disclosure can be used to deliver a cantharidin formulation to a subject as soon as skin has fully epithelized after previous treatment.

A formulation, delivery device or system of the present disclosure can be used to deliver a cantharidin formulation to a subject's skin which was untreated, previously treated or to be further treated. Some examples of previous treatment include, but are not limited to, removal of scar tissue, scabs or keratinized tissue via debriding, scrubbing, soaking or surgical excision. Previous treatment can also include cryotherapy, cauterization, the application or acids or bases, application of salicylic acid, lasers, surgical debridement, soaking, hydrogen peroxide or immunotherapy. Previous treatment can also include the application tape, creams, ointments, solutions, waxes or hydrophobic barriers to limit the area of skin that is exposed to the cantharidin formulation. A cantharidin formulation can be used prior to or concurrent with surgical resection, cryotherapy, cauterization, the application or acids or bases, application of acids, lasers, surgical debridement, soaking, hydrogen peroxide, immunotherapy or covering the treated area with an occlusive tape or bandage.

A cantharidin formulation and associated delivery device or system can be used to treat the following; Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer, Bowen's disease, Breast cancer, Buschke-Ollendorff syndrome, Cervical cancer, Cervical dysplasia, Cherry angiomas, Chondrodermatitis nodularis chronica helicis, Cutaneous endometriosis, Cutaneous Leukemia, Cutaneous Lymphoma, Cutaneous meningioma, Cutaneous myxoma, Darier's disease, Dermal dendrocyte hamartoma, dermatofibroma, Dermatofibrosarcoma protuberans, Eccrine angiomatous hamartoma, Ectodermal dysplasia. Epidermal inclusion cysts, Epidermal Naevi (including but not limited to nacvus scbaccous, Comedone nacvus, Proteus syndromebccker nacvus), Epithclioid cell histiocytoma, Familial myxovascular fibromas, Fungal skin disease (including Lobomycosis), Granular cell tumor, Glucaonoma syndrome, Genital warts, Ichthyosis (including but not limited to Ichthyosis vulgaris, Ichthyosis lamellaria, X-linked Ichthyosis, epidermolytic hyperkeratosis, Ichthyosis acquista and keratosis palmoplantaris), Idiopathic guttate hypomelanosis, Infantile acropustulosis, Infantile fibromatosis, Kaposi's sarcoma, Keloid, Keratoacanthoma, Keratocyst, Knuckle pads, Lentigo, Melanoma, Microvenular hemangioma, Morton's neuroma, Multifocal lymphangioendotheliomatosis, Multinucleate cell angiohistocytoma, Multiple cutaneous leciomyomas, Mycosis fungoides, Neuroma cutis, Neurothekeoma, Nevus flammeus, Nevus lipomatosus superficialis, Pachydermodactyly, Palisaded encapsulated neuroma, Parasitic skin diseases (including but not limited to Scabies, Pediculosis, Tungiasis, Hookwork-related cutaneous larva migrans), Pityriasis ruba pilaris, Piloleiomyomas, Plexiform fibrohistiocytic tumor, Porokeratotic eccrine ostial and Dermal duct nevus, Progressive nodular histiocytoma Psoriasis (including but not limited to Psoriatic erytroderma, Palmoplantat psoriasis, Palmoplantar pustolosis, Generalized pustular psoriasis of Zumbusch, Lingua geographical) Porokeratosis, Seborrhoeic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis or Zosteriform metastasis.

Other skin ailments can also be treated with a cantharidin formulation including, without limitation, Benign epidermal cysts, Birthmarks. Calluses, Corns, Eczema, Freckles, Moles, Pigmentation disorders (Drug induced hyperpigmentation, Dyschromatosis symmetrica hereditaria, Dyschromatosis universalis hereditaria, Familial progressive hyperpigmentation, Galli Galli disease, Hemosiderin hyperpigmentation, Idiopathic guttate hypomelanosis, Iron metallic discoloration, leukoderma, Melasma, Mukamel syndrome, Necklace of Venus, Nevus anemicus, Nevus depigmentosus, Pallister-Killian syndrome, Phylloid hypomelanosis, Piebaldism, Pigmentatio reticularis facici et colli, Pilar Cysts, Pityriasis alba, Poikiloderma of Civatte, Poikiloderma vasculare atrophicans, Postinflammatory hyperpigmentation, Progressive macular hypomelanosis, Pruritus, Reticular pigmented anomaly of the flexures, Reticulate acropigmentation of Kitamura, Riehl melanosis, Shah-Waardenburg syndrome, Shiitake mushroom dermatitis, Tar melanosis, Titanium metallic discoloration, Transient neonatal pustular melanosis, Vagabond's leukomelanoderma, Vasospastic macules, Wende-Bauckus syndrome, X-linked reticulate pigmentary disorder, Yemenite deafblind hypopigmentation syndrome), Scars, Skin tags, Tattoo removal or Vitiligo (including but not limited to non-segmented Vitiligo, and/or Segmented vitiligo trichome vitiligo, Quadrichrome vitiligo, Vitiligo ponctue).

There may also be a use for a cantharidin formulation in epidermal skin rejuvenation, such as a skin peel or exfoliation, in individuals with sun damage or wrinkles.

Due to its chemotactic properties, ability to induce cell arrest and apoptosis, vesicant activity and other therapeutic outcomes a cantharidin formulation may have utility in combination with surgical, radiographic, immunotherapeutic, small molecule based, antibody-based, recombinant protein based, nucleic acid-based or chemotherapeutic agents. A cantharidin formulation may also have utility in as a second-line, third-line or forth-line therapeutic to treat patients who have failed prior therapies. Examples for use of cantharidin formulations, devices, and methods of the present disclosure include: immediately following Mohs Micrographic surgery in treating Basal Cell Carcinoma or after the failure of systemic chemotherapeutic agents in treating Mycosis fungoides or in combination with destructive therapies such as cryotherapy or hydrogen peroxide or acids or ingenol mebutate in the treatment of Actinic kerotisis or as a first line therapy in the treatment of Porokeratosis or Seborrheic keratosis.

A formulation, delivery device or system of the present disclosure can be used to treat warts, *Molluscum*, Actinic keratosis, Seborrheic keratosis or other cutaneous hyperproliferative disorder that have failed or have been recalcitrant to prior therapy. Alternatively, a formulation, delivery device or system of the present disclosure can be used as a first-line therapy. Alternatively a formulation, delivery device or system of the present disclosure can be used in combination with another first line therapy.

A cantharidin formulation may be used to treat patients with cancer. For instance, a cantharidin formulation may be used to inhibit tumor growth and/or used to kill cancer cells directly. In some cases, a cantharidin formulation may be used to kill cancer stem cells. In some cases the cantharidin formulation may be used to treat benign cancerous lesions. For example, a cantharidin formulation may be used to kill cancer cells with a multi-drug resistant phenotype. In some situations, norcantharidin, cantharidimide, or norcantharimide or analogues of cantharidin may be utilized instead of cantharidin.

Cantharidin formulations, devices, systems, and methods can be used for other purposes, such as, for example, in the production of autologous or allogeneic skin that can used for skin grafts or as a blistering model for the testing of drugs or an approach for eliminating residual cancer cells following a surgical procedure.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for delivering a cantharidin formulation to a subject, comprising:
    a reservoir comprising a cavity containing a cantharidin formulation, wherein the cantharidin formulation comprises at least 0.001% (w/v) of cantharidin, acetone, ethanol, a gelling agent, and a film-forming agent; wherein the gelling agent is hydroxypropyl cellulose; the film-forming agent is nitrocellulose; and the cantharidin formulation is free of diethyl ether; and
    an applicator unit in fluid communication with the reservoir, wherein the reservoir holds a volume less than or equal to 10 milliliters (mL) of the cantharidin formulation.

2. The system of claim 1, wherein the cantharidin formulation comprises at least 0.5% (w/v) cantharidin.

3. The system of claim 1, wherein the cantharidin formulation comprises between 0.1% and 10% (w/v) of the film-forming agent.

4. The system of claim 1, wherein the applicator unit comprises a puncturable barrier on one end and a cap engaging the applicator unit to cover the puncturable barrier.

5. The system of claim 4, wherein the cap is a screw-on or snap-on cap.

6. The system of claim 4, wherein the cap is transparent.

7. The system of claim 4, wherein the cap comprises a puncture apparatus for punching through the barrier prior to use of the applicator unit.

8. The system of claim 1, wherein the opening of the applicator unit comprises a tip having a diameter less than or equal to 5 mm.

9. The system of claim 1, wherein the system provides for controlled delivery of the cantharidin formulation to the subject.

10. The system of claim 1, wherein the cantharidin formulation further comprises a flavorant that induces a bitter taste to prevent or deter licking and/or ingestion of the formulation by a subject.

11. The system of claim 10, wherein the flavorant is selected from the group consisting of denatonium, amarogentin, gentiopicrin, sucrose octaacetate, quercetin, brucine, and quassin.

12. The system of claim 1, further comprising a colorant selected from the group consisting of D&C violet, isosulfan blue, methylene blue, methyl red, methyl orange, congo red, alizarin yellow, bromocresol green, and gentian violet.

13. The system of claim 1, wherein the cantharidin formulation further comprises one or more plasticizers.

14. The system of claim 13, wherein the one or more plasticizers comprise camphor and castor oil.

15. The system of claim 1, wherein the cantharidin formulation has a Reynolds number less than 1500 at 25° C.

16. The system of claim 1, wherein the cantharidin formulation has a viscosity of more than 5 centipoise and less than 100 centipoise.

17. The system of claim 1, wherein the cantharidin formulation comprises 55% (w/v) or more of acetone; and 30% (w/v) or more of ethanol.

18. The system of claim 1, wherein the cantharidin formulation further comprises a colorant that enables visible detection of the formulation by the subject.

19. The system of claim 1, wherein the cantharidin formulation comprises:
    ethanol in an amount up to 99% (w/v);
    acetone in an amount up to 99% (w/v);
    hydroxypropyl cellulose in an amount up to 10% (w/v);
    nitrocellulose in an amount up to 10% (w/v);
    castor oil in an amount up to 5% (w/v);
    camphor in an amount up to 5% (w/v); and
    cantharidin in amount from 0.001-7% (w/v).

20. The system of claim 19, wherein the cantharidin formulation further comprises:
    denatonium benzoate in an amount from 0.00001-1% (w/v); and
    gentian violet in an amount from 0.00001-1% (w/v).

21. A method for delivering a cantharidin formulation to a subject for treating a condition susceptible to treatment with the cantharidin formulation, comprising:
providing an applicator device comprising a reservoir comprising the cantharidin formulation and an applicator unit comprising a channel in fluid communication with the reservoir; and
delivering the cantharidin formulation from the reservoir through the channel to the subject, wherein the cantharidin formulation comprises at least 0.001% (w/v) of cantharidin, acetone, ethanol, a gelling agent, and a film-forming agent; wherein the gelling agent is hydroxypropyl cellulose; the film-forming agent is nitrocellulose; and the cantharidin formulation is free of diethyl ether.

22. The method of claim 21, wherein the cantharidin formulation comprises at least 0.5% (w/v) cantharidin.

23. The method of claim 21, wherein the cantharidin formulation comprises between 0.1% and 10% (w/v) of the film-forming agent.

24. The method of claim 21, wherein the subject is diagnosed with a skin disease.

25. The method of claim 24, wherein the skin disease is an epithelial wart, a Molluscum lesion, actinic keratosis, or seborrheic keratosis.

26. The method of claim 24, wherein the skin disease is a common wart, genital wart, or plantar wart.

27. The method of claim 24, wherein the skin disease is Molluscum contagiosum.

28. The method of claim 24, wherein the skin disease is caused by human papilloma virus (HPV).

29. The method of claim 21, wherein the delivering comprises delivering less than or equal to 10 milliliters (mL) of the cantharidin formulation.

30. The method of claim 21, wherein the cantharidin formulation is administered in a time period that is less than or equal to 30 seconds.

31. The method of claim 21, wherein the delivery of the cantharidin formulation is controlled delivery.

32. The method of claim 21, wherein the cantharidin formulation has a viscosity of more than 5 centipoise and less than 100 centipoise.

33. The method of claim 21, wherein the cantharidin formulation comprises 55% (w/v) or more of acetone; and 30% (w/v) or more of ethanol.

34. The method of claim 21, wherein the cantharidin formulation comprises:
ethanol in an amount up to 99% (w/v);
acetone in an amount up to 99% (w/v);
hydroxypropyl cellulose in an amount up to 10% (w/v);
nitrocellulose in an amount up to 10% (w/v);
castor oil in an amount up to 5% (w/v);
camphor in an amount up to 5% (w/v); and
cantharidin in amount from 0.001-7% (w/v).

35. The method of claim 34, wherein the cantharidin formulation further comprises:
denatonium benzoate in an amount from 0.00001-1% (w/v); and
gentian violet in an amount from 0.00001-1% (w/v).

36. A kit for administering a cantharidin formulation to a subject, comprising:
a plurality of separately packaged, individually removable, dosage units in liquid or gel form, wherein the dosage units are in a packaging unit, and wherein the dosage units each comprise the cantharidin formulation in an amount from 0.01 mL to 10 mL, wherein the cantharidin formulation comprises at least 0.001% (w/v) of cantharidin, acetone, ethanol, a gelling agent, and a film-forming agent; wherein the gelling agent is hydroxypropyl cellulose; the film-forming agent is nitrocellulose; and the cantharidin formulation is free of diethyl ether;
the kit further comprising instructional material for administering the cantharidin formulation for treating a condition susceptible to treatment using the cantharidin formulation.

37. A formulation comprising:
at least 0.001% (w/v) of cantharidin;
acetone;
ethanol;
a film-forming agent, wherein the film-forming agent is nitrocellulose; and
a gelling agent, wherein the gelling agent is hydroxypropyl cellulose; and the formulation is free of diethyl ether.

38. The formulation of claim 37, wherein the formulation has a Reynolds number less than 1500 at 25° C.

39. The formulation of claim 37, further comprising a flavorant selected from the group consisting of denatonium, amarogentin, gentiopicrin, sucrose octaacetate, quercetin, brucine, and quassin.

40. The formulation of claim 37, further comprising a colorant selected from the group consisting of D&C violet, isosulfan blue, methylene blue, methyl red, methyl orange, congo red, alizarin yellow, bromocresol green, and gentian violet.

41. The formulation of claim 37, further comprising one or more plasticizers.

42. The formulation of claim 41, wherein the one or more plasticizers comprise camphor and castor oil.

43. The formulation of claim 37, wherein the formulation has a viscosity of more than 5 centipoise and less than 100 centipoise.

44. The formulation of claim 37, wherein the formulation comprises 55% (w/v) or more of acetone; and 30% (w/v) or more of ethanol.

45. The formulation of claim 37, wherein the formulation further comprises a flavorant that induces a bitter taste to prevent or deter licking and/or ingestion of the formulation by a subject.

46. The formulation of claim 37, wherein the formulation further comprises a colorant that enables visible detection of the formulation by the subject.

47. The formulation of claim 37, comprising:
ethanol in an amount up to 99% (w/v);
acetone in an amount up to 99% (w/v);
hydroxypropyl cellulose in an amount up to 10% (w/v);
nitrocellulose in an amount up to 10% (w/v);
castor oil in an amount up to 5% (w/v);
camphor in an amount up to 5% (w/v); and
cantharidin in amount from 0.001-7% (w/v).

48. The formulation of claim 47 further comprising:
denatonium benzoate in an amount from 0.00001-1% (w/v); and
gentian violet in an amount from 0.00001-1% (w/v).

* * * * *